United States Patent
Peeper et al.

(10) Patent No.: US 9,629,851 B2
(45) Date of Patent: Apr. 25, 2017

(54) ROCK IN COMBINATION WITH MAPK PATHWAY

(71) Applicant: Stichting Het Nederlands Kanker Instituut—Antoni van Leeuwenhoek Ziekenhuis, Amsterdam (NL)

(72) Inventors: Daniel Simon Peeper, Amsterdam (NL); Marjon Antoinetta Smit, Amsterdam (NL); Celia Jill Vogel, Amsterdam (NL)

(73) Assignee: STITCHING HET NEDERLANDS KANKER INSTITUT—ANTONI VAN LEEUWENHOEK ZIEKENHUIS, Amsterdam (NL)

( * ) Notice: Subject to any disclaimer, the term of this patent is extended or adjusted under 35 U.S.C. 154(b) by 0 days.

(21) Appl. No.: 15/023,229

(22) PCT Filed: Sep. 22, 2014

(86) PCT No.: PCT/NL2014/050648
§ 371 (c)(1),
(2) Date: Mar. 18, 2016

(87) PCT Pub. No.: WO2015/041533
PCT Pub. Date: Mar. 26, 2015

(65) Prior Publication Data
US 2016/0228451 A1  Aug. 11, 2016

(30) Foreign Application Priority Data

Sep. 20, 2013 (NL) ...................................... 2011480

(51) Int. Cl.
| | |
|---|---|
| *A61K 31/551* | (2006.01) |
| *A61K 38/00* | (2006.01) |
| *A61K 31/4184* | (2006.01) |
| *A61K 31/437* | (2006.01) |
| *A61K 31/4409* | (2006.01) |
| *A61K 31/4439* | (2006.01) |
| *A61K 31/506* | (2006.01) |
| *A61K 31/519* | (2006.01) |
| *A61K 31/5377* | (2006.01) |

(52) U.S. Cl.
CPC ........ *A61K 31/551* (2013.01); *A61K 31/4184* (2013.01); *A61K 31/437* (2013.01); *A61K 31/4409* (2013.01); *A61K 31/4439* (2013.01); *A61K 31/506* (2013.01); *A61K 31/519* (2013.01); *A61K 31/5377* (2013.01)

(58) Field of Classification Search
CPC .............. A61K 31/4184; A61K 31/437; A61K 31/4409; A61K 31/4439; A61K 31/506; A61K 31/519; A61K 31/5377
USPC ................................................. 514/19.2, 218
See application file for complete search history.

(56) References Cited

PUBLICATIONS

Greger J G et al.,"Combinations of BRAF, MEK and PI3K/mTOR Inhibitors Pvercome Acquired Resistance to the BRAF Inhibtor GSK2118436, Dabreafenib, Mediated by NRAS or MEK Mutations", Molecular Cancer Therapeutics, pp. 909-920, vol. 11, No. 4 (Apr. 2012).
C.M. Nijenhuis et al.,"Is combination therapy the next step to overcome resistance and reduce toxicities in melanoma?", Cancer Treatment Reviews, pp. 385-312, vol. 39, No. 4 (Jun. 2013).
Hidetoshi Sumimoto et al.,"Effective inhibition of cell growth and invasion of melanoma by combined suppression of BRAF (V599E) and Skp2 with lentiviral RNAi", International Journal of Cancer, pp. 472-476, vol. 18, No. 2 (2006).
Vahe Zohrabian et al., "Rho/ROCK and MAPK signaling pathways are involved in glioblastoma cell migration and proliferation" Anticancer Res., pp. 119-123, vol. 29, No. 1 (Jan. 2009).
Masahide Nakajima et al.,"Effect of Wf-536, a novel ROCK inhibitor, against metastasis of B16 melanoma", Cancer Chemotherapy and Pharmacology, pp. 319-324, vol. 52, No. 4 (Oct. 2003).
Alissa Routhier et al.,"Pharmacological inhibition of Rho-kinase signaling with Y-27632 blocks melanoma tumor growth" Oncology Reports, pp. 861-867, vol. 23, No. 3 (Mar. 2010).
H Ray-David et al., "RSK promotes G2 DNA damage checkpoint silencing and participates in melanoma chemoresistance",Oncogene, pp. 4480-4489, vol. 32, No. 38 (Oct. 2012).

*Primary Examiner* — Raymond Henley, III
(74) *Attorney, Agent, or Firm* — Browdy and Neimark, PLLC

(57) ABSTRACT

The current disclosure relates to pharmaceutical combinations and compositions useful in the treatment of certain types of cancer. The disclosure also relates to method of treatment these certain types of cancer. In particular, the disclosure relates to the combined use of inhibitors of ROCK and proteins of the MAPK/ERK-pathway in the treatment of KRAS-, NRAS- or BRAF-mutated cancer, in particular in NRAS mutated melanoma.

15 Claims, 8 Drawing Sheets

Figure 1D, top panel:
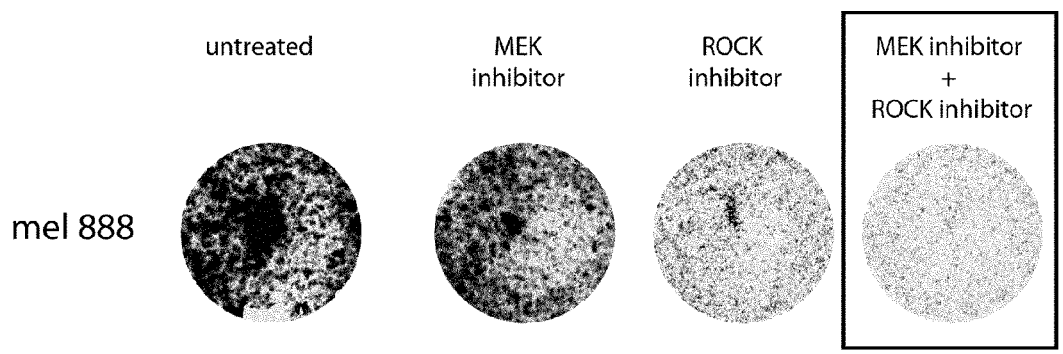
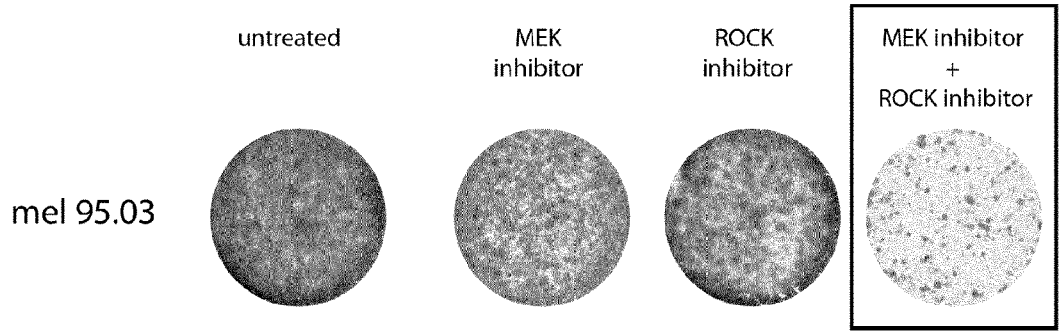

ROCK IN COMBINATION WITH MAPK PATHWAY

FIELD OF THE INVENTION

The current disclosure relates to pharmaceutical combinations and compositions useful in the treatment of certain types of cancer. The disclosure also relates to method of treatment these certain types of cancer. In particular, the disclosure relates to the combined use of inhibitors of ROCK protein and proteins of the MAPK/ERK-pathway in the treatment of KRAS-, NRAS- or BRAF-mutated cancer, in particular in NRAS mutated melanoma.

PRIOR ART

Cancer is one of the leading causes of death in the Europe and the United States. Despite recent advances in understanding mechanisms involved in cancer and in diagnosis and treatment, drug therapies for metastatic disease are often palliative in nature. Drug therapies seldom offer a long-term cure. There is a constant need for new methods of treatment, either in the form of monotherapy or in the form of combination treatment, combining different new or known drugs as first line therapy, and as second line therapies in treatment of resistant tumors.

Cancer cells are by definition heterogeneous. For example, multiple mutational mechanisms may lead to the development of cancer and mutational mechanisms associated with some cancers may differ between one tissue type and another; it is therefore often difficult to predict whether a specific cancer will respond to a specific chemotherapeutic (Cancer Medicine, 5th edition, Bast et al, B. C. Decker Inc., Hamilton, Ontario).

The treatment of cancer is gradually changing from an organ-centered to a pathway-centered approach. Cancer cells often have an addiction to the signals that are generated by the cancer-causing genes. Consequently, targeted cancer drugs that selectively inhibit the products of activated oncogenes can have dramatic effects on cancer cell viability. This approach has yielded significant clinical results for Non Small Cell Lung Cancer (NSCLC) having activating mutations in EGFR or translocations of the ALK kinase and for melanoma patients having a BRAF mutant tumor. However, this approach has not been successful in all type of cancers, in particular in cancers characterized by oncogenic mutations in one of the members of the RAS gene family, or in the BRAF. In particular treatment options of NRAS-mutated cancer, for example NRAS-mutated melanoma are limited.

It is therefore goal of the current invention to provide for new and improved methods of treatment of KRAS, BRAF and NRAS-mutated cancers, as well as to provide for products and therapeutically pharmaceutical combinations for use in such mutant cancers.

DESCRIPTION OF THE DRAWINGS

FIG. 1D: Combination of ROCK inhibitor Fasudil (top panel) or GSK269962A (bottom panel) with a MEK inhibitor kills or inhibits BRAF mutant melanoma cell proliferation. Cells were seeded equal densities and treated with GSK1120212 (MEKi) and GSK269962A (ROCKi) as indicated and stained with crystal violet.

DESCRIPTION

Definitions

Figure 1A:
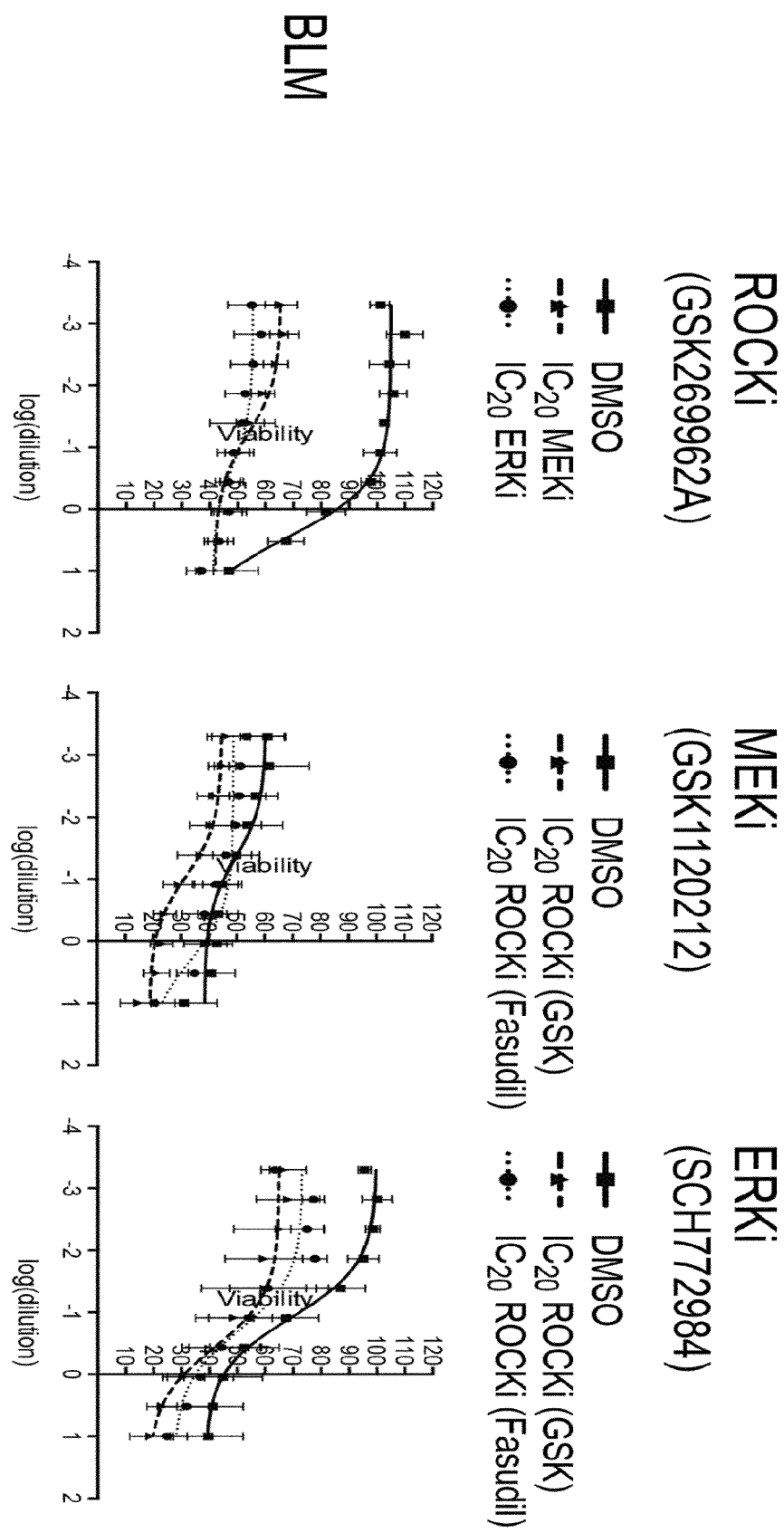
FIG. 1A: NRAS mutant melanoma cell lines are sensitive to combinations of ROCK and MEK or ERK inhibitors; Cells were treated with a dilution series of ROCK inhibitor (left panel), MEK inhibitor (middle panel) or ERK inhibitor (right panel) either alone or in combination with MEK/ERK/ROCK inhibitor as indicated. After 3 days total cell numbers were determined with a Cell Titer-Blue assay. The y-axis represents the percentage of living cells.
Figure 1A:
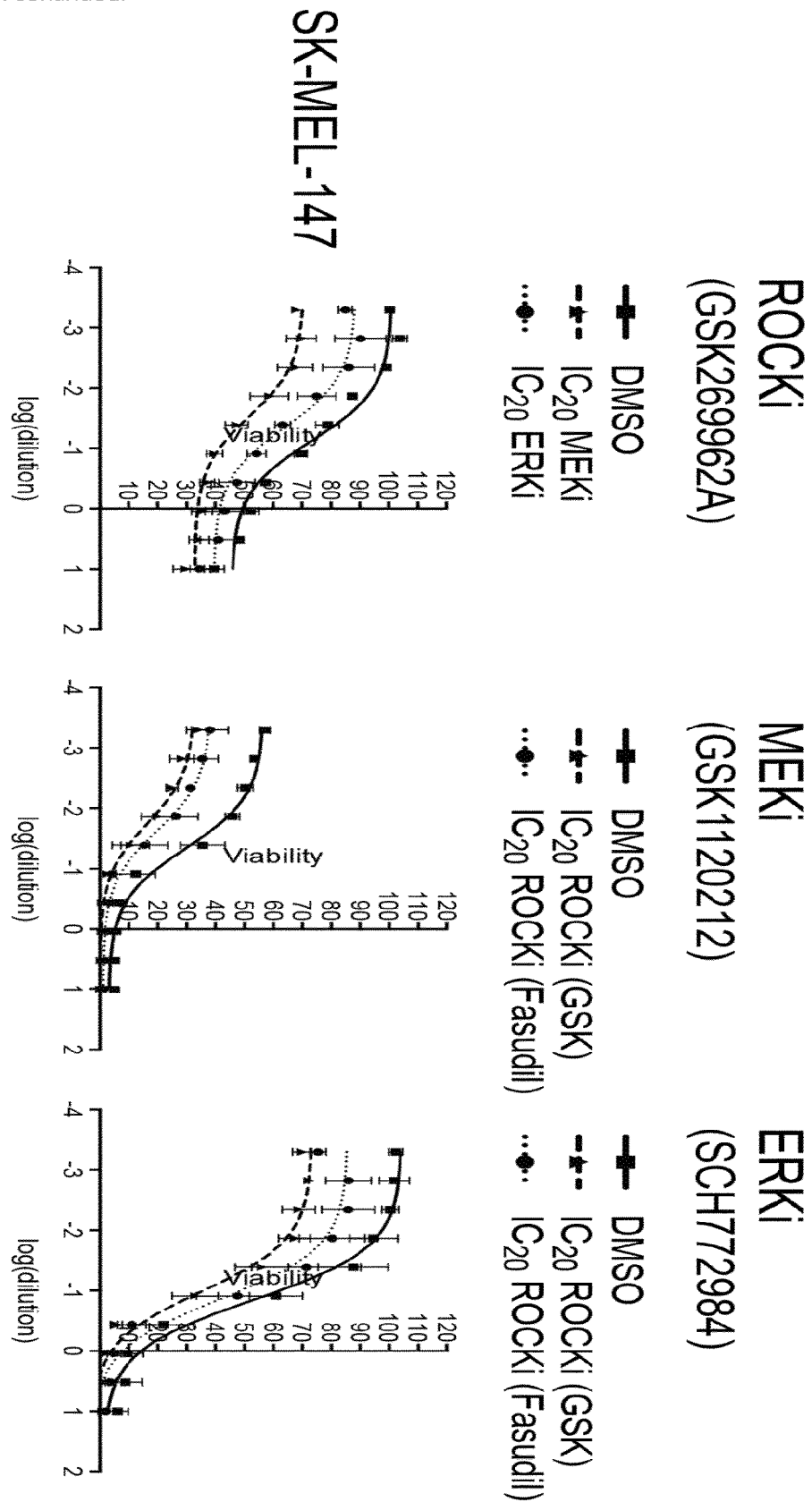

Unless defined otherwise, technical and scientific terms used herein have the same meaning as commonly understood by one of ordinary skill in the art to which this disclosure belongs. One skilled in the art will recognize many methods and materials similar or equivalent to those described herein, which could be used in the practice of the present invention. For example, conventional molecular biology, microbiology, and recombinant DNA techniques including sequencing techniques are well known among those skilled in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984). Indeed, the present invention is in no way limited to the methods and materials described.

For purposes of the present invention, the following terms are defined below.

As used herein, the singular forms "a," "an" and "the" include plural referents unless the context clearly dictates otherwise. For example, a method for administrating a drug includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases.

As used herein, the term "at least" a particular value means that particular value or more. For example, "at least 2" is understood to be the same as "2 or more" i.e., 2, 3, 4, 5, 6, 7, 8, 9, 10, 11, 12, 13, 14, 15, . . . , etc As used herein "cancer" and "cancerous" refer to or describe the physiological condition in mammals that is typically characterized by unregulated cell growth. The terms "cancer," "neoplasm," and "tumor," are used interchangeably and refer to cells that have undergone a malignant transformation that makes them pathological to the host organism. Primary cancer cells can be distinguished from non-cancerous cells by techniques known to the skilled person. A cancer cell, as used herein, includes not only primary cancer cells, but also cancer cells derived from such primary cancer cell, including metastasized cancer cells, and cell lines derived from cancer cells.

As is well known, tumors may metastasize from a first locus to one or more other body tissues or sites. Reference to treatment for a "neoplasm," "tumor" or "cancer" in a patient includes treatment of the primary cancer, and, where appropriate, treatment of metastases.

As used herein, "in combination with" is intended to refer to all forms of administration that provide a first drug together with a further (second, third) drug. The drugs may be administered simultaneous, separate or sequential and in any order. Drugs administered in combination have biological activity in the subject to which the drugs are delivered. Within the context of the invention, a combination thus comprises at least two different drugs, and wherein one drug is at least a ROCK-inhibitor and wherein the other drug is at least an inhibitor of another protein of the MAPK/ERK pathway, as disclosed herein in detail. In an embodiment, in the combination, the ROCK-inhibitor is a selective inhibitor, and does preferably does not inhibit the "another protein of the MAPK/ERK pathway", as disclosed herein in detail. In an embodiment, in the combination, the inhibitor of another protein of the MAPK/ERK pathway, as disclosed herein in detail, is a selective inhibitor, and within the context of the current invention, does not inhibit ROCK. In a further embodiment, in the combination, both the ROCK-inhibitor and the inhibitor of "another protein of the MAPK/ERK pathway", as disclosed herein in detail, are selective inhibitors.//pct A used herein "compositions", "products" of "combinations" useful in the methods of the present disclosure include those suitable for various routes of administration, including, but not limited to, intravenous, subcutaneous, intradermal, subdermal, intranodal, intratumoral, intramuscular, intraperitoneal, oral, nasal, topical (including buccal and sublingual), rectal, vaginal, aerosol and/or parenteral or mucosal application. The compositions, formulations, and products according to the disclosure invention normally comprise the drugs (alone or in combination) and one or more suitable pharmaceutically acceptable excipients or carriers.

As used herein, "to comprise" and its conjugations is used in its non-limiting sense to mean that items following the word are included, but items not specifically mentioned are not excluded. It also encompasses the more limiting "to consist of"."

As used herein, "an effective amount" is meant the amount of an agent/pharmaceutical compound required to ameliorate the symptoms of a disease relative to an untreated patient. The effective amount of active agent(s) used to practice the present invention for therapeutic treatment of a cancer varies depending upon the manner of administration, the age, body weight, and general health of the subject. Ultimately, the attending physician or veterinarian will decide the appropriate amount and dosage regimen. Such amount is referred to as an "effective" amount. Thus, in connection with the administration of a drug which, in the context of the current disclosure, is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

As used herein, in general the term "inhibitor" of a (defined) protein, for example ERK, refers to any compound capable of down-regulating, decreasing, suppressing or otherwise regulating the amount and/or activity of the (defined) protein, for example ERK. The inhibitors to be used in accordance with the present invention may be selective inhibitors of said (defined) protein; the term "selective" or "selectivity" expresses the biologic fact that at a given compound concentration enzymes (or proteins) are affected to different degrees. In the case of enzymes (or proteins) selective inhibition can be defined as preferred inhibition by a compound at a given concentration. In other words, an enzyme is selectively inhibited over another enzyme when there is a concentration which results in inhibition of the first enzyme whereas the second enzyme is not affected. To compare compound effects on different enzymes it is important to employ similar assay formats. For the proteins/ enzymes as disclosed herein, such assay formats are readily available in the prior art. Thus, within the context of the current invention the different drugs used in the combination may be drugs that selectively inhibit one of the proteins to be inhibited according to the invention in comparison to the other protein(s), for example when used in a clinical setting.

"Mammal" as used herein, refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term. Preferably the mammal is human.

"Pharmaceutically acceptable" is employed herein to refer to those combinations of a therapeutic as described herein, other drugs or therapeutics, materials, compositions, and/or dosage forms which are, within the scope of sound medical judgment, suitable for use in contact with the tissues of human beings and animals, without excessive toxicity, irritation, allergic response, or other problem or complication, commensurate with a reasonable benefit/risk ratio.

"Pharmaceutically-acceptable carrier", as used herein, means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

As used herein "simultaneous" administration refers to administration of more than one drug at the same time, but not necessarily via the same route of administration or in the form of one combined formulation. For example, one drug may be provided orally whereas the other drug may be provided intravenously during a patients visit to a hospital. "Separate" administration includes the administration of the drugs in separate form and/or at separate moments in time, but again, not necessarily via the same route of administration. "Sequentially" of "sequential administration" indicates that the administration of a first drug if followed, immediately or in time, by the administration of the second drug.

As used herein, "small molecule" is understood to refer to a chemical compound having a molecular weight below 2,500 Daltons, more preferably between 300 and 1,500 Daltons, and still more preferably between 400 and 1000 Daltons. It is preferred that these small molecules are organic molecules. In certain embodiments, "small molecule" does not include peptide or nucleic acid molecules.

The term "subject" is intended to include vertebrates, preferably a mammal, including human and non-human mammals such as non-human primates. Human subjects are can be referred to as patients.

As used herein, the terms "treat," "treating", "treatment," and the like refer to reducing or ameliorating a disorder and/or symptoms associated therewith. It will be appreciated that treating a disorder or condition does not require that the disorder, condition or symptoms associated therewith be completely eliminated.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Cancers that are either wild type or mutant for NRAS, KRAS or BRAF are identified by known methods. For example, wild type or mutant NRAS/BRAF/KRAS cancer cells can be identified by DNA amplification and sequencing techniques, DNA and RNA detection techniques, including, but not limited to Northern and Southern blot, respectively, and/or various biochip and array technologies. Wild type and mutant polypeptides can be detected by a variety of techniques including, but not limited to immunodiagnostic techniques such as ELISA, or Western blot. Mutation tests are, for example, available via fttp://therapy.collabrx.com/melanoma/molecular_analysis/(as per 27 Jul. 2013).

DETAILED DESCRIPTION

The current disclosure is based on the surprising finding that a combination of an inhibitor of the protein (enzyme) ROCK and at least one inhibitor of a protein of the MAPK/ERK pathway is co-operative and/or synergistic, i.e. produces an effect greater than the effect of the individual drugs, or even greater than the sum of the their individual effects, in inhibiting proliferation of or inducing apoptosis in a cancer in a mammal, preferably a human, wherein the cancer is selected from the group consisting of NRAS-, KRAS- and BRAF-mutated cancer, preferably NRAS-mutated cancer, for example, but not limited to NRAS-, KRAS- and BRAF-mutated melanoma, for example NRAS-mutated melanoma or lung cancer. The inhibitors in the combination may, in one embodiment be selective inhibitors, or a selective inhibitor. In addition, the claimed combination works also in those cells that are (relatively) insensitive to inhibition by inhibitors of a protein of the MAPK/ERK pathway alone (e.g. a RAF-inhibitor alone, an ERK-inhibitor alone, a MEK-inhibitor alone, or a p90RSK-inhibitor alone). Such cells are also referred to as resistant cancer cells and do not normally respond to treatment. The cancer may be resistant at the beginning of treatment (often called intrinsic resistance), or it may become resistant during treatment (often called acquired resistance, also called refractory cancer). In other words, in one embodiment the cancer is a NRAS-, KRAS- and BRAF-mutated cancer, preferably melanoma, that is or has become relatively insensitive or resistant to an inhibitor of a protein of the MAPK/ERK-pathway, preferably, that has become relatively insensitive or resistant to a ERK-inhibitor, a MEK-inhibitor, a p90RSk-inhibitor and/or a RAF-inhibitor, i.e. has or acquired resistance. The term "acquired resistance" indicates that the cancer becomes resistant to the effects of the drug after being exposed to it for a certain period of time.

The inventors of the present invention have demonstrated, via experiments, that the combination of a ROCK-inhibitor and at least one inhibitor of a protein of the MAPK/ERK pathway, for example a MEK-inhibitor, a ERK-inhibitor, a RAF-inhibitor or a p90RSK-inhibitor manifests an unexpected and co-operative and/or synergistic, therapeutic effect on the treatment of NRAS-, KRAS- and BRAF-mutated cancer, preferably NRAS-mutated cancer, for example, NRAS-mutated melanoma. The invention thus provides for improved treatment strategies by employing the combination at least two different drugs or compounds, directed to inhibiting the combination of proteins/enzymes as disclosed herein. This for the first time allows to optimize the drug treatment by specifically optimizing treatment so as to inhibit the combination of proteins/enzymes in the best possible way, for example by applying selective inhibitors.

For example, by the combination, the dose of each of the drugs in the combination may be optimized in order to achieve optimal treatment effect. For example the individual dose of a first individual drug in the combination may be optimized to achieve optimal inhibition of a first protein, and a second, third or further drug in the combination may be optimized to achieve optimal inhibition of the other protein/enzyme to be inhibited, and as detailed herein. In addition, the invention allows for the treatment with various and different combinations of inhibitors of the proteins/enzymes to be inhibited, as detailed herein. This is very useful in case, for example, for an individual patient, certain drugs or drug combinations are not well tolerated or lead to undesired further complications. The current invention allows for the replacement of a drug in such combination, or of the combination by another drug combination, in accordance with the invention and in order to overcome undesired effects or, again optimize treatment of the patient. In addition, when using the combination, the dose of the individual drugs may be lowered compared to when the drugs are used individually, which may be beneficial in view of toxicity.

The combination disclosed herein exhibits (therapeutic) co-operation and/or synergy when used to treat a subject or patient. Such effect may be demonstrated by the showing that the combination is superior to one or other of the constituents used as at a given, for example, optimum dose.

In a first aspect of the current disclosure, there is provided for a combination of a ROCK-inhibitor and an inhibitor of a protein of the MAPK/ERK pathway in the treatment of a cancer selected from the group consisting of NRAS-, KRAS- and BRAF-mutated cancer, preferably NRAS-mutated cancer.

The combination therapy disclosed herein is particular suitable for use in patients that carry mutations in the genes encoding a RAS protein and/or BRAF protein, leading to proteins with aberrant function.

The term "RAS protein" as used herein means any protein which is a member of the ras-subfamily, a subfamily of GTPases involved in cellular signaling. As is known in the art, activation of RAS causes cell growth, differentiation and survival. RAS proteins include, but are not limited to, HRAS, KRAS and NRAS. The proteins differ significantly only in the C-terminal 40 amino acids.

These proteins are GTPases that function as molecular switches regulating pathways responsible for proliferation and cell survival. RAS proteins are normally tightly regulated by guanine nucleotide exchange factors (GEFs) promoting GDP dissociation and GTP binding and GTPase-activating proteins (GAPs) that stimulate the intrinsic GTPase activity of RAS to switch off signaling. Aberrant RAS function is associated with hyper-proliferative developmental disorders and cancer and in tumors is associated with a single mutation typically at codons 12, 13 or 61. A comprehensive overview of RAS mutations in cancer was reported by Prior et al (2012) Cancer Res; 2457-67.

The combination therapy disclosed herein is suitable for use in patients with KRAS-mutated (also referred to as or KRAS-mutant) cancer, and in a preferred embodiment particular useful in patients that are characterized by having a KRAS-mutant melanoma. The term "KRAS-mutated cancer", and thus KRAS-mutated melanoma are well known to the skilled person. A comprehensive overview of RAS mutations, including KRAS-mutations, in cancer was reported by Prior et al (2012) Cancer Res; 2457-67. KRAS-mutant cells promote oncogenesis due to being mutationally activated, in most cases, at codon 12, 13 and 61. In total forty-four separate point mutations have been characterized in RAS isoforms, with 99.2% in codons 12, 13 and 61. The protein product of the normal KRAS gene performs an essential function in normal tissue signaling, and the mutation of a KRAS gene is an essential step in the development of many cancers.

The GTPase KRAS, also known as V-Ki-ras2 Kirsten rat sarcoma viral oncogene homolog or KRAS, is a protein that in humans is encoded by the KRAS gene (e.g. Gene accession number 3845; Refseq RNA Accessions NM_004985.3; protein NP_004976.2). Like other members of the Ras family, the KRAS protein is a GTPase and is an early player in many signal transduction pathways. KRAS acts as a molecular on/off switch. Once it is turned on it recruits and activates proteins necessary for the propagation of growth factor and other receptors' signal, such as c-Raff and PI 3-kinase.

In a preferred embodiment, the combination therapy disclosed herein is for use in patients with NRAS-mutated (also referred to as or NRAS-mutant) cancer, and in a preferred embodiment particular useful in patients that are characterized by having a NRAS-mutated melanoma. The term "NRAS-mutated cancer" and therefore NRAS-mutated melanoma are well known to the skilled person. A comprehensive overview of RAS mutations, including NRAS-mutations, in cancer was reported by Prior et al (2012) Cancer Res; 2457-67. NRAS-mutant cells promote ontogenesis due to being mutationally activated, in most cases, again at codon 12, 13 and 61.

The NRAS protein is a GTPase enzyme that in humans is encoded by NRAS (neuroblastoma RAS viral (v-ras) oncogene homolog) gene gene (e.g. Gene accession number 4893; Refseq RNA Accessions NM_002524.4; protein NP_002515.1). The N-ras gene specifies two main transcripts of 2 Kb and 4.3 Kb, both transcripts appear to encode identical proteins as they differ only in the 3' untranslated region.

The combination therapy disclosed herein is suitable for use in patients with BRAF-mutated (also referred to as or BRAF-mutant) cancer, and in a preferred embodiment particular useful in patients that are characterized by having a BRAF-mutant melanoma. The term "BRAF-mutated cancer" and therefore BRAF-mutated melanoma are well known to the skilled person. BRAF (e.g. Gene accession number 673; Refseq RNA Accessions NM_004333.4; protein NP_004324.2), is a member of the RAF family, which includes ARAF and CRAF in humans (Ikawa, Mol Cell Biol. 8(6):2651-4 (1988)). BRAF is a serine/threonine protein kinase and participates in the RAS/RAF/MEK/ERK mitogen activated protein kinase pathway (MAPK pathway, see Williams & Roberts, Cancer Metastasis Rev. 13(1):105-16 (1994); Fecher et al 2008 Curr Opin Oncol 20, 183-189 or Cargnello M, Roux P P. Microbiol Mol Biol Rev. 2011 March; 75(1):50-83). Approximately 40-60% of (cutaneous) melanomas carry a mutation in the BRAF protein. Approximately 90% of these mutations result in the substitution of glutamic acid for valine at codon 600 (BRAF V600E, although other mutations are also known (e.g. BRAF V600K and BRAF V600R). Such mutation in BRAF typically leads to proliferation and survival of melanoma cells (Davies et al Nature 2002; 417:949-54; Curtin et al N Engl J Med 2005; 353:2135-47), through activation of the MAPK/ERK pathway. As is well-known to the skilled person, this pathway plays a significant role in modulating cellular responses to extracellular stimuli, particularly in response to growth factors, and the pathway controls cellular events including cell proliferation, cell-cycle arrest, terminal differentiation and apoptosis (Peyssonnaux et al., Biol Cell. 93(I-2):53-62 (2001)).

The amino acid sequence of BRAF, NRAS or KRAS protein and any other protein mentioned herein, and variations thereof are available in GenBank, accessible via http://www.ncbi.nlm.nih.gov/genbank/.

The disclosed combination comprises a ROCK-inhibitor and at least one inhibitor of a protein of the MAPK/ERK pathway. The skilled person is well aware of such ROCK-inhibitors and such inhibitors of a protein of the MAPK/ERK pathway, as these are readily available in the scientific literature or in various patent documents.

Within the context of the current disclosure a ROCK-inhibitor comprises both an inhibitor of ROCK1 and/or of ROCK2. Rho-associated protein kinase (ROCK) is a kinase belonging to the AGC (PKA/PKG/PKC) family of serine-threonine kinases. It is mainly involved in regulating the shape and movement of cells by acting on the cytoskeleton. Details on ROCKs, and their function are reviewed by Morgan-Fisher et al (2013) J Histochem Cytochem 61(3) 185-198. The two ROCKs, ROCK I (also known as p160ROCK and ROKβ) and ROCK II (Rho-kinase and ROKα), are 160-kDa proteins encoded by distinct genes. The mRNA of both kinases is ubiquitously expressed, but the ROCK I protein is mainly found in organs such as liver, kidney, and lung, whereas ROCK II protein is mainly found in muscle and brain. The amino acid sequences of the two ROCKs are highly homologous (~65%), and they exhibit the same overall domain structure.

The ROCKs were first identified almost 20 years ago and were suggested to be regulators of the actin cytoskeleton downstream of Rho. Since then, a range of interaction partners for ROCKs have been identified, many of which are linked to regulation of the actin cytoskeleton, including ezrin/radixin/moesin (ERM), the LIM-kinases (LIMK), myosin light chain (MLC), and MLC-phosphatase (MLCP).

By ROCK activity is meant any function of ROCK, such as regulation of the cytoskeleton through the phosphorylation of downstream substrates, leading to increased actin filament stabilization and generation of actin-myosin contractility.

By ROCK inhibitor is meant a compound that reduces the biological activity of ROCK (either ROCK 1 or ROCK 2, e.g. Genbank Accession No. NM-005406 or e.g. Genbank Accession No. NM_004850); or that reduces the expression of an mRNA encoding a ROCK polypeptide; or that reduces the expression of a ROCK polypeptide.

Mammalian cells encode two Rho kinases, ROCK1 and ROCK2. These kinases are activated by binding to an active, GTP-bound Rho GTPase. As discussed above, ROCK phosphorylates a number of substrates on serine or threonine residues. These substrates are involved in a wide range of cell behavior. For example, myosin light chain phosphatase, involved in stress fiber formation and contractility; LIM kinase, involved in actin stabilization; NHE1 involved in focal adhesions and actin; and PTEN and Ezrin (Mueller et al., Nat. Rev. Drug Discov. 4:387-398, 2005; Riento et al., Nat. Rev. Mol. Cell Biol. 4:446-456, 2003). ROCK inhibitors such as Y-27632 and Fasudil bind to the catalytic site in the kinase domain and displace ATP.

As used herein, an "effective amount of an inhibitor", e.g. an "effective amount of a ROCK inhibitor" is the amount of inhibitor required to inhibit expression of ROCK or inhibit activity of ROCK. For example, in the case of ROCK inhibitor, when the ROCK inhibitor is a small molecule, antibody or negative regulator of ROCK, an effective amount is the concentration required to partially or completely eliminate ROCK activity, such as its kinase activity. The activity of a (potential) ROCK inhibitor may be established using assays described in the art. For example, preference is given to ROCK inhibitors that in the inhibition assay for ROCK described in EP2542528 inhibit ROCK with an IC50 value of less than 100 μm, 10 μM, preferably less than 1 μM.

ROCK inhibitors are known to those skilled in the art, and such inhibitors as suggested in the art are described herein and are in use in clinical trials for the treatment of several clinical conditions. These include Fasudil which is currently in use in Japan for treatment of cerebral vasospasm after subarachnoid hemorrhage. Other ROCK inhibitors have been through phase I and II trials for glaucoma and spinal cord injury, examples include Wf-536, Y-27632, and RKI-1447 and Slx-2119.

In one embodiment, the ROCK inhibitor is a small molecule. Exemplary small molecule ROCK inhibitors described in the art include Y-27632 (U.S. Pat. No. 4,997, 834) and Fasudil (also known as HA 1077; Asano et al., J. Pharmacol. Exp. Ther. 241:1033-1040, 1987).

Other small molecules reported to specifically inhibit ROCK include H-1152 ((S)-(+)-2-Methyl-1-[(4-methyl-5-isoquinolinyl)sulfonyl]homopiperazine, Ikenoya et al., J. Neurochem. 81:9, 2002; Sasaki et al., Pharmacol. Ther. 93:225, 2002); N-(4-Pyridyl)-N'-(2,4,6-trichlorophenyl)urea (Takami et al., Bioorg. Med. Chem. 12:2115, 2004); and 3-(4-Pyridyl)-1H-indole (Yarrow et al., Chem. Biol. 12:385, 2005).

Additional small molecule Rho kinase inhibitors include those described in WO 03/059913, WO 03/064397, WO 05/003101, WO 04/112719, WO 03/062225, WO 07/042321 and WO 03/062227; U.S. Pat. No. 7,217,722 and U.S. Pat. No. 7,199,147; and U.S. 2003/0220357, U.S. 2006/0241127, U.S. 2005/0182040 and U.S. 2005/0197328; and EP2542528, EP2597953. A non-limitative overview of well-known ROCK inhibitors is provided in Table 1 (Some of which also described in: Fasudil: Ying et al., Mol. Cancer Ther. 5:2158, 2006; Y27632: Routhier et al., Oncol. Rep. 23:861, 2010; Y39983: Tanihara et al., Clin. Sciences 126: 309, 2008; RKI-1447: Patel et al., Cancer Res. 72: 5025, 2012; GSK269962A: Doe et al., J Pharm. Exp. Ther. 320: 89, 2007).

TABLE 1

Examples or ROCK-inhibitors:

| Compound name | CAS number | formula | remarks |
|---|---|---|---|
| AMA-0076 | | | |
| AMA-0247 | | | |
| AR-12286 | | | |
| AR-13324 | | | |
| AS-1892802 | | | |
| ATS-8535 | | | |

TABLE 1-continued

Examples or ROCK-inhibitors:

| Compound name | CAS number | formula | remarks |
|---|---|---|---|
| ATS-907 | | | |
| BA-1037 | | | |
| BA-1049 | | | |
| CCG-1423 | 285986-88-1 | C18H13ClF6N2O3 | |
| Cethrin | | | |
| DE-104 | | | |
| DE-104 | | | |
| GSK2699662 | 850664-21-0 | C29H30N8O5 | |
| GSK429286 | 864082-47-3 | C21H16F4N4O2 | |
| H1152P | 451462-58-1 | C16H21N3O2S•2HCl | |
| HA1077 (Fasudil) | 103745-39-7 | C14H17N3O2S•2HCl | |
| HA1100 hydrochloride (hydroxyfasudil) | 105628-72-6 | C14H17N3O3S•HCl | |
| HMN-1152 | | | |
| K-115 | | | |
| Ki-23095 | | | |
| Rho Inhibitor | | C20H18N6O | |
| Rhosin | | | |
| Rho kinase inhibitor | | | Kalypsys/Alcon; IDDBCP260624 |
| rho kinase inhibitor | | | Bayer |
| Rho Kinase Inhibitor II | 97627-27-5 | C12H8Cl3N3O | |
| Rho Kinase Inhibitor III | 7272-84-6 | C13H10N2 | |
| Rho Kinase Inhibitor IV | 913844-45-8 | C18H24N4O3S•2HCl•H2O | |
| Rho Kinase Inhibitor V | 1072906-02-5 | C18H15N3O3 | |
| Rho Kinase Inhibitor VII | | C21H24N8 | |
| Rho kinase inhibitors | | | Amakem/Halo BioConsulting |
| Rho-kinase inhibitor | | | Kowa |
| Rhostatin | | | |
| RKI1447 (ROCK Inhibitor XIII) | 1342278-01-6 | C16H14N4O2S•CH3SO3H | |
| ROCK inhibitor | | | Devgen |
| ROCK inhibitors | | | Bayer-Schering Pharma |
| ROKalpha inhibitors | | | BioFocus |
| SAR407899 | | | |
| SB772077B dihydrochloride | 607373-46-6 | C15H18N8O2•2HCl | |
| SR 3677 dihydrochloride | 1072959-67-1 | C22H24N4O4•2HCl | |
| Thiazovivin | 1226056-71-8 | C15H13N5OS | |
| WF-536 | 539857-64-2 | C14H15N3O•ClH | |
| XD-4000 series | | | |
| Y27632 | 146986-50-7 | C14H21N3O•2HCl•H2O | |
| Y39983 | 471843-75-1 | C16H16N4O•HCl | |

In particular examples, the ROCK inhibitor is a small interfering nucleotide sequence capable of inhibiting ROCK activity, such as siRNA using one or more small double stranded RNA molecules. For example, ROCK activity in a cell can be decreased or knocked down by exposing (once or repeatedly) the cell to an effective amount of the appropriate small interfering nucleotide sequence. The skilled person knows how to design such small interfering nucleotide sequence, for example as described in handbooks such as Doran and Helliwell RNA interference: methods for plants and animals Volume 10 CABI 2009. A variety of techniques can be used to assess interference with ROCK activity of such small interfering nucleotide sequence, such as described in WO 2005/047542, for example by determining whether the candidate small interfering nucleotide sequence decreases ROCK activity. Candidate small interfering nucleotide sequences that are capable of interference may be selected to further analysis to determine whether they also inhibit proliferation of melanoma cells, for example by assessing whether changes associated with inhibition of proliferation of melanoma cells occurs in melanoma cells.

The inhibitor of a protein of the MAPK/ERK pathway may be any inhibitor that reduces the activity of one or more proteins that belong to the MAPK/ERK pathway.

The MAPK/ERK pathway is well-known to the skilled person and is one of the four parallel mitogen activated protein kinase (MAPK) signaling pathways identified: ERK1/ERK2, JNK, p38 and ERK5.

The pathways are involved in cellular events such as growth, differentiation and stress responses (J. Biol. Chem. (1993) 268, 14553-14556). These four pathways are linear kinase cascades in that MAPKKK phosphorylates and activates MAPKK, and MAPKK phosphorylates and activates MAPK. To date, seven MAPKK homologs (MEK1, MEK2, MKK3, MKK4/SEK, MEK5, MKK6, and MKK7) and four MAPK families (ERK1/2, JNK, p38, and ERK5) have been identified. Activation of these pathways regulates the activity of a number of substrates through phosphorylation. These substrates include: transcription factors such as TCF, c-myc, ATF2 and the AP-1 components, fos and Jun; cell surface components EGF-R; cytosolic components including PHAS-I, p90rsk, cPLA2 and c-Raf-1; and cytoskeleton components such as tau and MAP2. MAPK signaling cascades are involved in controlling cellular processes including proliferation, differentiation, apoptosis, and stress responses.

Of the known MAPK signaling pathways, the MAPK/ERK pathway (also referred to as RAF-MEK-ERK pathway or Ras-Raf-MEK-ERK pathway) mediates proliferative and anti-apoptotic signaling from growth factors and oncogenic factors such as Ras and Raf mutant phenotypes that promote tumor growth, progression, and metastasis. By virtue of its central role in mediating the transmission of growth-promoting signals from multiple growth factor receptors, the MAPK/ERK pathway provides molecular targets with potentially broad therapeutic applications in, for example, cancerous and noon-cancerous hyperproliferative disorders, immunomodulation and inflammation.

Within the context of the current invention a protein of the MAPK/ERK pathway includes ERK, MEK, RAF, and RSK proteins, as discussed below.

In a preferred embodiment, the protein of the MAPK/ERK pathway is selected from the group consisting of RAF, MEK, ERK, and p90RSK, and combination of two, three or four thereof. Thus in a preferred embodiment, the inhibitor of a protein of the MAPK/ERK pathway is selected from the group consisting of a RAF-inhibitor, an ERK-inhibitor, a MEK-inhibitor and a p90RSK-inhibitor.

In a preferred embodiment more than one inhibitor of a protein of the MAPK/ERK pathway is used. For example, two, three or four inhibitors of one or more proteins of the MAPK/ERK pathway are used in the combination therapy disclosed herein, i.e. in combination with a ROCK inhibitor or one, two, three or more ROCK inhibitors. For example, at least one ROCK-inhibitor may be combined with at least one MEK-inhibitor and/or at least one ERK-inhibitor, and/or at least one p90RSK inhibitor.

A RAF protein, polypeptide or peptide is to indicate a polypeptide having serine/threonine protein kinase activity. RAF kinases are a family of three serine/threonine-specific protein kinases that are related to retroviral oncogenes. The three RAF kinase family members are ARAF (A-RAF; for example Genbank Accession NO: NP001243125), BRAF (B-RAF) and CRAF (C-RAF; for example Genbank Accession NO: NP002871).

For example, BRAF (for example, Genbank Accession NO: NP004324) phosphorylates and activates MEK (MEK1 and MEK2). BRAF (or BRAF) is a member of the RAF family, which includes ARAF and CRAF in humans (Ikawa, Mol Cell Biol. 8(6):2651-4 (1988)). BRAF is a serine/threonine protein kinase and participates in the RAS/RAF/MEK/ERK mitogen activated protein kinase pathway (MAPK pathway, see Williams & Roberts, Cancer Metastasis Rev. 13(1):105-16 (1994); Fecher et al 2008 Curr Opin Oncol 20, 183-189).

CRAF (e.g. Gene accession number 5894; Refseq RNA Accessions NM_002880.3; protein NP_002871.1) acts as a MAP3 kinase, initiating the entire kinase cascade of the MAPK/ERK pathway.

These amino acid sequence of BRAF, CRAF and ARAF enzymes, other proteins mentioned herein, and variations thereof are available in GenBank, accessible via http://www.ncbi.nlm.nih.gov/genbank/ by entering either the numbers mentioned above or entering the relevant protein name.

By RAF biological activity is meant any function of RAF, such as enzymatic activity, kinase activity, or signaling the MAPK/ERK pathway.

By RAF inhibitor, for example a BRAF inhibitor, is meant a compound that reduces the biological activity of RAF, for example BRAF; or that reduces the expression of an mRNA encoding a RAF polypeptide, for example BRAF; or that reduces the expression of a RAF polypeptide, for example BRAF. RAF kinase inhibitors as used herein include efficient inhibitors of RAF kinase, particularly CRAF kinase inhibitors and wild and mutated BRAF kinase inhibitors, e.g. including inhibitors of mutant BRAF kinase.

RAF kinase inhibitors, e.g. low molecular compounds, are known to the skilled person. Any RAF inhibitor, including any pharmaceutical agent having RAF inhibitory activity or selective RAF inhibitors may be utilized in the present invention. Examples of RAF kinase inhibitors include the compounds GW5074, BAY 43-9006, CHIR-265, and compounds as defined in U.S. Pat. No. 6,987,119, WO98022103, WO99032436, WO2006/084015, WO2006/125101, WO2007/027855, WO2005/004864, WO2005/028444, WO03082272, WO2005/032548, and WO2007030377, WO2005028444, WO03082272, WO2005032548, and WO2007030377. BRAF inhibitors are described, for instance, in WO 2010/114928, WO 2005/123696, WO2007/002325, WO 2006/003378, WO 2006/024834, WO 2006/024836, WO 2006/040568, WO 2006/067446 and WO 2006/079791, WO02/24680 and WO03/022840, WO 2005/047542, AU 2003/286447, US 2004/0096855, AU2002/356323, WO2005089443, WO2006/053201, US20050267060, WO2008120004, US20090181371, WO2008120004 which patent applications can be referenced to the extent of their disclosure of BRAF inhibitors and methods of making and using the same.

Preferred RAF inhibitors include Vemurafenib, PLX4720 (Tsai et al. 2008 PNAS 105(8):3041), PLX4032 (RG7204), GDC-0879 (Klaus P. Hoeflich et al. Cancer Res. 2009 Apr. 1; 69:3042-3051), PLX-4720, Sorafenib Tosylate (e.g. from Bayer and Onyx Pharmaceuticals as Nexavar), dasatinib (also known as BMS-354825, e.g. as produced by Bristol-Myers Squibb and sold under the trade name Sprycel), erlotinib (e.g. as marketed by Genentech and OSI pharmaceuticals as Tarceva), LGX818 from Novartis, Dabrafenib (Tafinlar™ capsule, made by GlaxoSmithKline, LLC), or a derivative thereof Preferably, the derivative of the BRAF inhibitor is a salt. Thus, according to the invention the RAF inhibitor may be selected from the group consisting of dasatinib, erlotinib hydrochloride, dabrafenib, gefitinib, imatinib mesilate, lapatinib, sorafenib tosylate and sunitinib malate. Preferably the RAF inhibitor is sorafenib tosylate. Particularly preferred is Vemurafenib (also known as PLX4032, RG7204 or RO5185426, e.g. marketed as Zelboraf, from Plexxikon (Daiichi Sankyo group) and Hoffmann-La Roche).

In one embodiment the RAF inhibitor is selected from any one of the BRAF inhibitors disclosed in WO2006/024834, WO2006/067446, PCT/GB2006/004756, or is selected from any one of CHIR-265 (Novartis), XL281 (Exelixis) or PLX4032 (Plexxikon, or Roche). In one embodiment the RAF inhibitor is selected from any one of the BRAF inhibitors disclosed in WO2008120004. Other BRAF inhibitors include GSK2118436, benzenesulfonamide, N-[3-[5-(2-amino-4-pyrimidinyl)-2-(1,1-dimethylethyl)-4-thiazolyl]-2-fluorophenyl]-2,6-difluoro-, methanesulfonate (1:1), N-{3-

[5-(2-aminopyrimidin-4-yl)-2-(1,1-dimethylethyl)thiazol-4-yl]-2-fluorophenyl}-2,6-difluorobenzenesulfonamide monomethanesulfonate (Clin Cancer Res. 2011; doi: 10.1158/1078-0432; http://www.ama-assn.org/resources/doc/usan/dabrafenib.pdf). A non-limitative overview of well-known RAF inhibitors is provided in Table 2.

binds activated and/or mutated BRAF such as the ones described in WO 2005/047542, or as described in US 2004/0096855.

A RAF inhibitor has RAF inhibitor activity, or in other words reduces activated (or mutated) RAF activity, which

TABLE 2

Examples or RAF-inhibitors:

| compound name | cellular target(s) | CAS number | formula |
|---|---|---|---|
| AZ 628 | wild-type c-Raf, B-Raf V600E | 878739-06-1 | C27H25N5O2 |
| CEP-32496 | B-Raf V600E, wild type B-Raf, c-Raf, Abl-1, CSF-1R | 1188910-76-0 | C24H22F3N5O5 |
| GDC 0879 | B-Raf (B-Raf V600E) | 905281-76-7 | C19H18N4O2 |
| GSK2118436, Dabrafenib | | 1195765-45-7 | C23H20F3N5O2S2 |
| GW 5074 | c-Raf | 220904-83-6 | C15H8Br2INO2 |
| L-779,450 | c-Raf (maybe also A-Raf?) | 303727-31-3 | C20H14ClN3O |
| MLN-2480, BIIB-024 | | 1096708-71-2 | C17H12Cl2F3N7O2S |
| NVP-BHG712 | c-Raf, c-Src, c-Abl, EphB4, VEGFR2 | 940310-85-0 | C26H20F3N7O |
| PF-04880594 | B-Raf, c-Raf | 1111636-35-1 | C19H16F2N8 |
| PLX-4720 | B-Raf V600E, c-Raf-1 Y340D/Y341D | 918505-84-7 | C17H14ClF2N3O3S |
| PLX4032, Vemurafenib, Zelboraf, RG7204, RO5185426 | B-Raf V600E, C-Raf, ACK1, FGR, KHS1, SRMS | 918504-65-1 | C23H18ClF2N3O3S |
| RAF265, CHIR-265 | B-Raf, C-Raf, VEGFR | 927880-90-8 | C24H16F6N6O |
| Regorafenib, BAY 73-4506, Fluoro-Sorafenib | c-Raf, VEGFR1, VEGFR2, VEGFR3, PDGFRβ, Kit, RET | 755037-03-7 | C21H15ClF4N4O3 |
| RO5126766 | Raf/MEK1/2 | | |
| SB 590885 | B-Raf (10fold more potent than for C-Raf) | 405554-55-4 | C27H27N5O2 |
| Sorafenib Tosylate, Nexavar, Bay 43-9006 | c-Raf, B-Raf, VEGFR-2, PDGFR-beta | 475207-59-1 | C21H16ClF3N4O3·C7H8O3S |
| ZM 336372 | c-Raf, (B-Raf 10fold less) | 208260-29-1 | C23H23N3O3 |

In particular examples, the RAF inhibitor is a small interfering nucleotide sequence capable of inhibiting RAF activity, such as siRNA using one or more small double stranded RNA molecules. For example, RAF activity in a cell can be decreased or knocked down by exposing (once or repeatedly) the cell to an effective amount of the appropriate small interfering nucleotide sequence. The skilled person knows how to design such small interfering nucleotide sequence, for example as described in handbooks such as Doran and Helliwell RNA interference: methods for plants and animals Volume 10 CABI 2009. A variety of techniques can be used to assess interference with RAF activity of such small interfering nucleotide sequence, such as described in WO 2005/047542, for example by determining whether the candidate small interfering nucleotide sequence decreases BRAF activity. Candidate small interfering nucleotide sequences that are capable of interference may be selected to further analysis to determine whether they also inhibit proliferation of melanoma cells, for example by assessing whether changes associated with inhibition of proliferation of melanoma cells occurs in melanoma cells.

The RAF inhibitor according to the present invention may be a binding agent such as an antibody which specifically activity may be verified by method known to the skilled person, for example those disclosed in EP0986382B1.

A ERK polypeptide or peptide is to indicate a polypeptide having serine/threonine protein kinase activity, e.g. ERK phosphorylates and activates MAP (microtubule-associated proteins), and having at least 85% amino acid identity to the amino acid sequence of a human ERK, e.g to ERK1 (e.g. Gene accession number 5595; Refseq RNA Accessions NM_001040056.2; protein NP_001035145.1) or ERK2 (e.g. Gene accession number 5594; Refseq RNA Accessions NM_002745.4; protein NP_002736.3). The amino acid sequence of ERK enzymes, other proteins mentioned herein, and variations thereof are available in GenBank, accessible via http://www.ncbi.nlm.nih.gov/genbank/ by entering either the numbers mentioned above or entering the relevant protein name.

By ERK biological activity is meant any function of ERK, such as enzymatic activity, kinase activity, the ability to phosphorylate an ERK substrate, or signaling the MAPK/ERK pathway.

By ERK inhibitor is meant a compound that reduces the biological activity of ERK; or that reduces the expression of an mRNA encoding an ERK polypeptide; or that reduces the expression of an ERK polypeptide. An ERK inhibitor can inhibit one member, several members or all members of the family of ERK kinases.

ERK (extracellularly regulated kinase) is a group of MAP kinases which regulate the growth and proliferation of cells (Bokemeyer et al. 1996, Kidney Int. 49, 1187).

Embodiments of the invention include an ERK inhibitor that inhibits or reduces ERK protein expression, amount of ERK protein or level of ERK translation, amount of ERK transcript or level of ERK transcription, stability of ERK protein or ERK transcript, half-life of ERK protein or ERK transcript, prevents the proper localization of an ERK protein or transcript; reduces or inhibits the availability of ERK polypeptide, reduces or inhibits ERK activity; reduces or inhibits ERK, binds ERK protein, or inhibits or reduces the post-translational modification of ERK, including its phosphorylation. In analogy, the above described inhibitory action are also to be construed to apply, in comparable fashion to any inhibitor described herein for its specific target (e.g. a BRAF inhibitor for BRAF, a ROCK inhibitor for ROCK etc.). In some embodiments the inhibitor is a selective inhibitor.

In some embodiments of the present invention, the ERK inhibitor is an ERK inhibitor such as disclosed in WO2002058687, for example SL-327 (Carr et al Psychopharmacology (Berl). 2009 January; 201(4):495-5060).

Further ERK inhibitors may be found in WO2002058687, AU2002248381, US20050159385, US2004102506, US2005090536, US2004048861, US20100004234, HR20110892, WO2011163330, TW200934775, EP2332922, WO2011041152, US2011038876, WO2009146034, HK1117159, WO2009026487, WO2008115890, US2009186379, WO2008055236, US2007232610, WO2007025090, and US2007049591. Reference is made to said documents with respect to their content regarding MEK inhibitors, and methods for making the same.

Examples or ERK-inhibitors are also shown in Table 3 below.

TABLE 3

ERK inhibitors

| compound name | cellular target(s) | CAS number | formula |
|---|---|---|---|
| BVD-523 | ERK1/2 | | |
| FR 180204 | ERK1/2 | 865362-74-9 | C18H13N7 |
| Hypothemycin | | 76958-67-3 | C19H22O8 |
| MK-8353, SCH900353 | ERK1 | | |
| Pluripotin | ERK1, Ras-GAP | 839707-37-8 | C27H25F3N8O2 |
| SCH772984 | ERK1/2 | 942183-80-4 | C34H34N8O2 |
| VX-11e, ERK-11e, TCS ERK 11e | ERK2 | 896720-20-0 | C24H20Cl2FN5O2 |

In particular examples, the ERK inhibitor is a small interfering nucleotide sequence capable of inhibiting ERK activity, such as siRNA using one or more small double stranded RNA molecules. For example, ERK activity in a cell can be decreased or knocked down by exposing (once or repeatedly) the cell to an effective amount of the appropriate small interfering nucleotide sequence. The skilled person knows how to design such small interfering nucleotide sequence, for example as described in handbooks such as Doran and Helliwell RNA interference: methods for plants and animals Volume 10 CABI 2009. Candidate small interfering nucleotide sequences that are capable of interference may be selected to further analysis to determine whether they also inhibit proliferation of melanoma cells, for example by assessing whether changes associated with inhibition of proliferation of melanoma cells occurs in melanoma cells.

The skilled person knows that analogues, derivatives or modified versions of the above-documented ERK inhibitors may be used in the context of the present invention, as long as such analogues, derivatives or modified versions have ERK inhibitor activity.

The ERK inhibitor according to the present invention may be a binding agent such as an antibody which specifically binds ERK, thereby inhibiting its function.

ERK inhibitor activity may be assayed in vitro, in vivo or in a cell line. In vitro assays include assays that determine inhibition of either the kinase activity or ATPase activity of activated ERK. Alternate in vitro assays quantitate the ability of the inhibitor to bind to ERK and may be measured either by radiolabelling the inhibitor prior to binding, isolating the inhibitor/ERK complex and determining the amount of radiolabel bound, or by running a competition experiment where new inhibitors are incubated with ERK bound to known radioligands. One may use any type or isoform of ERK, depending upon which ERK type or isoform is to be inhibited. An example of measuring ERK inhibitory activity is described in EP 1317453 B1.

A MEK polypeptide (e.g. Gene accession numbers 5604 or 5605; Refseq RNA Accessions NM_002755.3 or NM_030662.3; protein NP_002746.1 or NP_109587.1), protein or peptide is to indicate a polypeptide having serine/threonine protein kinase activity. For example MEK1 (e.g. Genbank Accession NO: NP002746) and MEK2 (e.g. Genbank Accession NO: NP109587) phosphorylates and activates MAPK. Another example is MEK3 ((e.g. Genbank Accession NO: NP002747). MEK comprises both MEK1 and MEK2: MAP/ERK kinase 1, MEK1, PRKMK1, MAPKK1, MAP2K1, MKK1 are the same enzyme, known as MEK1, MAP/ERK kinase 2, MEK2, PRKMK2, MAPKK2, MAP2K2, MKK2 are the same enzyme, known as MEK2. MEK1 and MEK2, together MEK, can phosphorylate serine, threonine and tyrosine residues in protein or peptide substrates. To date, few cellular substrates of MEK isoforms have been identified. The amino acid sequence of MEK enzymes, other proteins mentioned herein, and variations thereof are available in GenBAnk, accessible via http://www.ncbi.nlm.nih.gov/genbank/ by entering either the numbers mentioned above or entering the relevant protein name.

By MEK biological activity is meant any function of MEK, such as enzymatic activity, kinase activity, or signaling the MAPK/ERK pathway.

By MEK inhibitor is meant a compound that reduces the biological activity of MEK; or that reduces the expression of an mRNA encoding a MEK polypeptide; or that reduces the expression of a MEK polypeptide. A MEK inhibitor can inhibit one member, several members or all members of the family of MEK kinases. In one embodiment the MEK inhibitor is a selective inhibitor.

Preferred MEK inhibitors, already known in the art, include but are not limited to the MEK inhibitors PD184352 and PD98059, inhibitors of MEKI and MEK2 U0126 (see Favata, M., et al., Identification of a novel inhibitor of mitogen-activated protein kinase. J. Biol. Chem. 273, 18623, 1998) and SL327 (Carr et al Psychopharmacology (Berl). 2009 January; 201(4):495-506), and those MEK inhibitors discussed in Davies et al (2000) (Davies et al Biochem J. 351, 95-105). In particular, PDI 84352 (Allen, Lee et al Seminars in Oncology, October 2003, pp. 105-106, vol. 30) has been found to have a high degree of specificity and potency when compared to other known MEK inhibitors, and may thus be preferred. A preferred MEK inhibitor GSK1120212/Trametinib (GlaxxoSmithKline) has been approved for treatment of BRAF mutant melanoma under the name Mekinist. MEK162 (Novartis) is also preferred. Other MEK inhibitors and classes of MEK inhibitors are described in Zhang et al. (2000) Bioorganic & Medicinal Chemistry Letters; 10:2825-2828.

Further MEK inhibitors are for example described in Tecle et al Medicinal Chemistry Letters Volume 19, Issue 1, 1 Jan. 2009, Pages 226-229; WO2009018238, WO2007/044084, WO2005/051300, WO2011/095807, WO2008124085, WO2009018233, WO2007113505, US2011105521, WO2011067356, WO2011067348, US2010004247, and US2010130519. Reference is made to said documents with respect to their content regarding MEK inhibitors, and methods for making the same. GSK1120212 is an example of a further MEK inhibitor.

The MEK inhibitor may also preferably be selected from AZD6244, 4-(4-Bromo-2-fluorophenylamino)-N-(2-hydroxyethoxy)-1,5-dimethyl-6-oxo-1,6-dihydropyridazine-3-carboxamide or 2-(2-fluoro-4-iodophenylamino)-N-(2-hydroxyethoxy)-1,5-dimethyl-6-oxo-1,6-dihydropyridine-3-carboxamide. In one embodiment the MEK inhibitor is selected from AZD6244 or a pharmaceutically acceptable salt thereof. In one embodiment the MEK inhibitor is AZD6244 hydrogen sulphate salt. AZD6244 hydrogen sulphate salt and derivates thereof may be synthesized according to the process described in WO2007/076245.

In another embodiment the MEK inhibitor is selected from 6-(4-Bromo-2-chloro-phenylamino)-7-fluoro-3-methyl-3H-benzoimidazole-5-carboxylic acid (2-hydroxy-ethoxy)-amide or a pharmaceutically acceptable salt thereof. In one embodiment the MEK inhibitor is 6-(4-Bromo-2-chloro-phenylamino)-7-fluoro-3-methyl-3H-benzoimidazole-5-carboxylic acid (2-hydroxy-ethoxy)-amide hydrogen sulphate salt. 6-(4-Bromo-2-chloro-phenylamino)-7-fluoro-3-methyl-3H-benzoimidazole-5-carboxylic acid (2-hydroxy-ethoxy)-amide hydrogen sulphate salt may be synthesized according to the process described in International Patent Publication Number WO2007/076245.

Furthermore, according to the invention the MEK inhibitor may be selected from the group consisting of certain experimental compounds, some of which are currently in Phase 1 or Phase II studies, namely PD-325901 (Phase 1, Pfizer), XL518 (Phase 1, Genentech), PD-184352 (Allen and Meyer Semin Oncol. 2003 October; 30(5 Suppl 16): 105-16.), PD-318088 (Tecle et al nic & Medicinal Chemistry Letters Volume 19, Issue 1, 1 Jan. 2009, Pages 226-229), AZD6244 (Phase II, Dana Farber, AstraZeneca) and Cl-1040 (Lorusso et al Journal of clinical oncology 2005, vol. 23, no 23, pp. 5281-5293).

In one embodiment the MEK inhibitor is selected from any one of AZD6244 (Example 10 of WO03/077914) or a pharmaceutically acceptable salt thereof, 2-(2-fluoro-4-iodophenylamino)-N-(2-hydroxyethoxy)-1,5-dimethyl-6-oxo-1 JS-dihydropyridine-3-carboxamide or a pharmaceutically acceptable salt thereof, 4-(4-Bromo-2-fluorophenylamino)-N-(2-hydroxyethoxy)-1,5-dimethyl-6-oxo-1,6-dihydropyridazine-3-carboxamide or a pharmaceutically acceptable salt thereof, PD-0325901 (Pfizer), PD-184352 (Pfizer), XL-518 (Exelixis), AR-119 (Ardea Biosciences, Valeant Pharmaceuticals), AS-701173 (Merck Serono), AS-701255 (Merck Serono), 360770-54-3 (Wyeth).

Examples of drugs that inhibit MEK include, PD-0325901 (Pfizer), AZD-8330 (AstraZeneca), RG-7167 (Roche/Chugai), RG-7304 (Roche), CIP-137401 (Cheminpharma), WX-554 (Wilex; UCB), SF-2626 (Semafore Pharmaceuticals Inc), RO-5068760 (F Hoffmann-La Roche AG), RO-4920506 (Roche), G-573 (Genentech) and G-894 (Genentech), N-acyl sulfonamide prodrug GSK-2091976A (GlaxoSmithKline), BI-847325 (Boehringer Ingelheim), WYE-130600 (Wyeth/Pfizer), ERK1-624, ERK1-2067, ERK1-23211, AD-GL0001 (ActinoDrug Pharmaceuticals GmbH), selumetinib (AZD6244), trametinib, TAK-733, Honokiol, MEK-162, derivates, and salts thereof.

Examples of MEK-inhibitors are shown in Table 4

TABLE 4

MEK-inhibitors

| compound name | CAS number | formula |
| --- | --- | --- |
| 10Z-Hymenialdisine, SK&F 108752 | 82005-12-7 | C11H10BrN5O2 |
| Arctigenin | 7770-78-7 | C21H24O6 |
| AST03026, Pimasertib, MSC1936369B | 1236699-92-5 | C15H15FIN3O3 |
| AZD6244, ARRY-14288, Selumetinib | 606143-52-6 | C17H15BrClFN4O3 |
| AZD8330, ARRY-424704, ARRY-704 | 869357-68-6 | C16H17FIN3O4 |
| CI-1040, PD 184352 | 212631-79-3 | C17H14ClF2IN2O2 |
| GDC-0973, XL518, XL 518, XL-518 | 934660-93-2 | C22H22F3IN2O2 |
| GSK1120212, JTP-74057, trametinib, Mekinist | 871700-17-3 | C26H23FIN5O4 |
| MEK162, Arry-162 | 606143-89-9 | C17H15BrF2N4O3 |
| PD 0325901 | 391210-10-9 | C16H14F3IN2O4 |
| PD 184352 | 212631-79-3 | C17H14ClF2IN2O2 |
| PD 198306 | 212631-61-3 | C18H16F3IN2O2 |
| PD 318088 | 391210-00-7 | C16H13BrF3IN2O4 |
| PD 98059 | 167869-21-8 | C16H13NO3 |
| RDEA119, Refametinib, BAY 869766, BAY86-9766 | 923032-37-5 | C19H20F3IN2O5S |
| RO4987655 | | |
| RO5126766 | | |
| SL327 | 305350-87-2 | C16H12F3N3S |
| TAK-733, TAK733 | 1035555-63-5 | C17H15F2IN4O4 |
| U0126 | 1173097-76-1 | C18H16N6S2 |
| WX-554 | | |

In another embodiment the MEK inhibitor may inhibit (gene) expression of MEK, for example by interfering with mRNA stability or translation. In one embodiment the MEK inhibitor is selected from small interfering RNA (siRNA), which is sometimes known as short interfering RNA or silencing RNA, or short hairpin RNA (shRNA), which is sometimes known as small hairpin RNA. The skilled person knows how to design such small interfering nucleotide sequence, for example as described in handbooks such as Doran and Helliwell RNA interference: methods for plants and animals Volume 10 CABI 2009.

The MEK inhibitor according to the present invention may be a binding agent such as an antibody which specifically binds MEK, thereby inhibiting its function.

A number of assays for identifying kinase inhibitors, including MEK inhibitors, are known, for example from Downey et al. (1996) J Biol Chem.; 271(35): 21005-21011 or EP2496575.

A p90RSK polypeptide (e.g. EC 2.7.11.1; e.g. Gene accession numbers 6195, 6197, 6196, or 27330; Refseq RNA Accessions NM_001006665, NM_002953, NM_004586, NM_001006932, NM_021135, or NM_014496; protein NP_001006666.1, NP_004577.1, NP_001006933.1, or NP_055311.1), protein or peptide is to indicate a protein of the ribosomal s6 kinase (rsk) a family of protein kinases. There are two subfamilies of rsk, p90RSK, also known as MAPK-activated protein kinase-1 (MAPKAP-K1), and p70RSK, also known as S6-H1 Kinase or simply S6 Kinase. There are three variants of p90RSK in humans, RSK 1-3. RSKs are serine/threonine kinases and are activated by the MAPK/ERK pathway. The RSK protein is a MAP kinase activated protein kinase (MAPKAP kinase) and described in, e.g., Leukemia, 17: 1263-1293 (2003). p90RSK is phosphorylated and activated by Erk1 and -2 in response to many growth factors, polypeptide hormones and neurotransmitters. RSK has been shown to directly promote cell survival by regulating the expression and activation of pro-survival proteins such as CREB (cyclic adenosine monophosphate response element binding protein). The combination of promoting cell survival and prevention of apoptosis by p90RSK causes excessive cell survival, eventually leading to diseases such as cancer and autoimmune disorders.

It has been found that p90RSK2 is overexpressed in more than 50% of human breast cancers, validating the family as a potential target for drug design.

The amino acid sequence of p90RSK enzyme, or other proteins mentioned herein, and variations thereof are available in GenBank, accessible via http://www.ncbi.nlm.nih.gov/genbank/ by entering either the numbers mentioned above or entering the relevant protein name.

By p90RSK biological activity is meant any function of p90RSK, such as herein. By p90RSK inhibitor is meant a compound that reduces the biological activity of p90RSK; or that reduces the expression of an mRNA encoding a p90RSK polypeptide; or that reduces the expression of a p90RSK polypeptide.

Non-limitative examples of p90RSK inhibitors include, for example, Kaempherol-3-O-(4'-O-acetyl-a-L-rhamnopyranoside), or those disclosed in EP1845778. Further examples are provided in the Table 5 below. The activity of RSK protein or inhibitory activity of a p90RSK inhibitor can be determined by the method described in, e.g., EMBO J., 14: 674-684 (1995) or in EP1845778. The inhibitor may, in one embodiment, be a selective inhibitor.

TABLE 5 p90RSK inhibitors

| compound name | CAS number | formula |
| --- | --- | --- |
| BI-D1870 | 501437-28-1 | C19H23F2N5O2 |
| BRD 7389 | 376382-11-5 | C24H18N2O2 |
| FMK | 821794-92-7 | C18H19FN4O2 |
| HH-5709 | 185313-17-1 | |
| IDDBCP287099 | | |
| IDDBCP292177 | | |
| SL 0101-1, SL-010, SL-0101-1 | 77307-50-7 | C25H24O12 |

In another embodiment the p90RSK inhibitor may inhibit (gene) expression of p90RSK, for example by interfering with mRNA stability or translation. In one embodiment the p90RSK inhibitor is selected from small interfering RNA (siRNA), which is sometimes known as short interfering RNA or silencing RNA, or short hairpin RNA (shRNA), which is sometimes known as small hairpin RNA. The skilled person knows how to design such small interfering nucleotide sequence, for example as described in handbooks such as Doran and Helliwell RNA interference: methods for plants and animals Volume 10 CABI 2009.

The p90RSK inhibitor according to the present invention may be a binding agent such as an antibody which specifically binds p90RSK, thereby inhibiting its function.

The person skilled in the art will understand that any combination as disclosed herein may be present in the combination as disclosed herein.

The combination therapy disclosed herein is useful in the treatment of patients having a cancer selected from the group consisting of NRAS-, KRAS- and BRAF-mutated cancers. However, the combination is in particular useful in the treatment of patients having melanoma, i.e. NRAS-mutated melanoma, KRAS-mutated-melanoma or BRAF-mutated melanoma. In a preferred embodiment the combination treatment is for patients with NRAS-mutated melanoma. The cancer, e.g. melanoma, e.g. NRAS mutant melanoma, maybe a naïve cancer (previously untreated with anti-cancer drugs, e.g. with an inhibitor on the MAPK/ERK pathway; another inhibitor, chemotherapy or Radiation therapy), or may be a cancer that is resistant or acquired resistance as a consequence of prior treatment (e.g. with an inhibitor on the MAPK/ERK pathway; another inhibitor, chemotherapy or Radiation therapy), as can be witnessed from the examples disclosed herein. The findings support a combination therapy of inhibitors of the MAPK/ERK pathway and ROCK inhibitors for NRAS, KRAS and/or BRAF mutated cancers, in particular NRAS mutant melanoma, both treatment-naïve and with acquired resistance to MAPK/ERK pathway, e.g. ERK pathway, targeting therapies.

In some embodiments, the combination disclosed herein and the use of the disclosed combination in the treatment of the type of cancers disclosed herein may further be combined with other drugs or treatments, for example with (the use of) chemotherapy and/or radio therapy.

Melanoma is, next to basal cell cancer and squamous cell cancer, one of the three most serious types of skin cancer. Skin cancer is the most commonly diagnosed type of cancer. Although less common than the other two types, melanoma causes the majority (75%) of deaths related to skin cancer (Jerant et al 2000 Am Fam Physician 62 (2): 357-68, 375-6, 381-2). Worldwide, about 160,000 new cases of melanoma are diagnosed yearly. It occurs more frequent in women than in men and is particularly common among Caucasians living in sunny climates, with high rates of incidence in Australia, New Zealand, North America, Latin America, and northern Europe (Parkin et al 2005 CA Cancer J Clin 55 (2): 74-108). According to a WHO report, melanoma cause about 48,000 deaths worldwide per year (Lucas et al 2006 Environmental Burden of Disease Series. 13. World Health Organization. ISBN 92 4 159440 3).

The first sign of melanoma often is a change in size, shape, color or feel of a mole, which may accordingly have turned into a malignant tumor of melanocytes. The present invention relates to combinations suitable for treating or lessening the severity of melanoma, including subtypes of melanoma such as but not limited to superficial spreading melanoma, nodular melanoma, lentigo maligna melanoma, acral lentiginous melanoma, and choroidal intraocular melanoma, ocular intraocular melanoma, and uveal intraocular melanoma.

Melanocytes are cells that normally produce the pigment melanin, which is responsible for brownish tint of skin. They predominantly occur in skin, but are also found in other parts of the body, such as in the bowel and the eye (uveal melanoma). Melanoma can occur in any part of the body where melanocytes are present.

Cutaneous melanomas have mutations in the NRAS GTPase in 15% of cases (NRAS mutated cancer, NRAS mutated melanoma; Kelleher et. al (2012 Cancer J. 18(2): 132-136)). Compared to melanomas with BRAF mutations, or melanomas "wild-type" for BRAF and NRAS, melanomas with NRAS mutations are more likely to be thicker tumors and to have a higher mitotic rate. Preclinical studies indicate that melanoma cells with NRAS mutations are dependent on NRAS for survival and proliferation, making NRAS an attractive therapeutic target in melanoma. However, to date, therapeutic strategies for NRAS mutant melanomas have not been realized in the art.

In an embodiment of the combination disclosed herein, the ROCK-inhibitor is selected from the group consisting of GSK269962A, Fasudil, RKI-1447, and Y27632; the RAF-inhibitor is selected from the group consisting of PLX4720 (Vemurafenib), and GSK2118436 (Dabrafenib); the ERK-inhibitor is selected from the group consisting of SCH772984 and VTX-11e; the MEK-inhibitor is selected from the group consisting of GSK1120212 (Trametinib) and MEK162; and/or the p90RSK-inhibitor is BI-D1870.

Also provided is a ROCK-inhibitor for use in treatment of a cancer selected from the group consisting of NRAS-, KRAS- and BRAF-mutated cancer, preferably NRAS-mutated cancer, wherein the ROCK-inhibitor is administrated simultaneously, separately or sequentially with an inhibitor of a protein of the MAPK/ERK pathway. In a preferred embodiment there is provided a ROCK-inhibitor for use in treatment of a cancer selected from the group consisting of NRAS-, KRAS- and BRAF-mutated cancer, preferably NRAS-mutated cancer, wherein said inhibitor of a protein of the MAPK/ERK pathway is selected from the group consisting of a RAF-inhibitor, an ERK-inhibitor, a p90RSK-inhibitor and a MEK-inhibitor.

Likewise is provided for a RAF-inhibitor for use in treatment of a cancer selected from the group consisting of NRAS-, KRAS- and BRAF-mutated cancer, preferably NRAS-mutated cancer, wherein the RAF-inhibitor is administrated simultaneously, separately or sequentially with a ROCK-inhibitor.

Accordingly, there is provided for an ERK-inhibitor for use in treatment of a cancer selected from the group consisting of NRAS-, KRAS- and BRAF-mutated cancer, preferably NRAS-mutated cancer, wherein the ERK-inhibitor is administrated simultaneously, separately or sequentially with a ROCK-inhibitor.

In addition, there is provided for a MEK-inhibitor for use in treatment of a cancer selected from the group consisting of NRAS-, KRAS- and BRAF-mutated cancer, preferably NRAS-mutated cancer, wherein the MEK-inhibitor is administrated simultaneously, separately or sequentially with a ROCK-inhibitor.

Also provided is a p90RSK-inhibitor for use in treatment of a cancer selected from the group consisting of NRAS-, KRAS- and BRAF-mutated cancer, preferably NRAS-mutated cancer, wherein the p90RSK-inhibitor is administrated simultaneously, separately or sequentially with a ROCK-inhibitor.

In preferred embodiments of the ROCK-inhibitor, RAF-inhibitor, ERK-inhibitor, MEK-inhibitor or p90RSK-inhibitor for use in treatments disclosed above, the ROCK-inhibitor is selected from the group consisting of GSK269962A, Fasudil, RKI-1447, and Y27632; the RAF-inhibitor is selected from the group consisting of PLX4720 (Vemurafenib), and GSK2118436 (Dabrafenib); the ERK-inhibitor is selected from the group consisting of SCH772984 and VTX-11e; the MEK-inhibitor is selected from the group consisting of GSK1120212 (Trametinib) and MEK162; and/or the p90RSK-inhibitor is BI-D1870.

In a preferred embodiment of the use, the cancer is NRAS mutated melanoma.

The inhibitors for the combination therapy as disclosed herein may be administered to the patient either simultaneously, separately or sequentially with the other drug(s) of the combination. For example, in practice the product leaflet of the ROCK-inhibitor may suggest the simultaneous, separate or sequential use of the ROCK-inhibitor with an inhibitor of a protein of the MAPK/ERK-pathway, preferably an ERK inhibitor and/or a MEK-inhibitor and/or a RAF-inhibitor and/or a p90RSK-inhibitor.

In another example, in practice the product leaflet of the inhibitor of a protein of the MAPK/ERK pathway (preferably an ERK inhibitor and/or a MEK-inhibitor and/or a RAF-inhibitor and/or a p90RSK-inhibitor) may suggest the simultaneous, separate or sequential use of the inhibitor of a protein of the MAPK/ERK pathway with a ROCK-inhibitor.

As explained above, the new use of the combination of inhibitors is not limited to combinations administered separately, but also includes the compositions obtained by physical association of the drugs and in either case a synergistic effect is obtained.

As used herein "simultaneous" administration refers to administration of more than one drug at the same time, but not necessarily via the same route of administration or in the form of one combined formulation. For example, one drug may be provided orally whereas the other drug may be provided intravenously during a patients visit to a hospital. Separate includes the administration of the drugs in separate form and/or at separate moments in time, but again, not necessarily via the same route of administration. Sequentially indicates that the administration of a first drug if followed, immediately or in time, by the administration of the second drug.

The combination of drugs disclosed herein will preferably be administered to the patient in a form that is suitable for administration to the patient and in a dose that is efficacious, i.e. in an effective amount, The current disclosure thus relates, in these aspects, to a combination therapy, wherein during the therapy the patient is treated with a drug that is an inhibitor of ROCK in combination with (another) inhibitor that inhibits a protein of the MAPK/ERK pathway, preferably an ERK-inhibitor, a MEK-inhibitor, a RAF-inhibitor and/or a p90RSK-inhibitor.

In another aspect of the invention there is provided for a product comprising a ROCK-inhibitor and an inhibitor of a protein of the MAPK/ERK pathway, as a combined preparation for simultaneous, separate or sequential use in treatment of a cancer selected from the group consisting of NRAS-, KRAS- and BRAF-mutated cancer, preferably NRAS-mutated cancer, even more preferably NRAS-mutated melanoma. In a preferred embodiment, said inhibitor of a protein of the MAPK/ERK pathway is selected from the group consisting of a RAF-inhibitor, an ERK-inhibitor, a MEK-inhibitor and a p90RSK-inhibitor. In another preferred embodiment, the ROCK-inhibitor is selected from the group consisting of GSK269962A, Fasudil, RKI-1447, and Y27632; the RAF-inhibitor is selected from the group consisting of PLX4720 (Vemurafenib), and GSK2118436 (Dabrafenib); the ERK-inhibitor is selected from the group consisting of SCH772984 and VTX-11e; the MEK-inhibitor is selected from the group consisting of GSK1120212 (Trametinib) and MEK162; and/or the p90RSK-inhibitor is BI-D1870.

In another aspect of the invention there is provided for use of a ROCK-inhibitor in the manufacture of a medicament for the treatment of a cancer selected from the group consisting of NRAS-, KRAS- and BRAF-mutated cancer, preferably NRAS-mutated cancer, wherein the treatment comprises the simultaneous, separate or sequential administration of the ROCK-inhibitor and a an inhibitor of a protein of the MAPK/ERK pathway.

Also provided is use of an inhibitor of a protein of the MAPK/ERK pathway in the manufacture of a medicament for the treatment of a cancer selected from the group consisting of NRAS-, KRAS- and BRAF-mutated cancer, preferably NRAS-mutated cancer, wherein the treatment comprises the simultaneous, separate or sequential administration of a ROCK-inhibitor and the inhibitor of a protein of the MAPK/ERK pathway.

Preferably, said inhibitor of a protein of the MAPK/ERK pathway is selected from the group consisting of a RAF-inhibitor, an ERK-inhibitor, a MEK-inhibitor and a p90RSK inhibitor. Preferably, the cancer is melanoma, preferably NRAS-mutated melanoma. Preferably, the ROCK-inhibitor is selected from the group consisting of GSK269962A, Fasudil, RKI-1447, Y27632; the RAF-inhibitor is selected from the group consisting of PLX4720 (Vemurafenib), and GSK2118436 (Dabrafenib); the ERK-inhibitor is selected from the group consisting of SCH772984 and VTX-11e; the MEK-inhibitor is selected from the group consisting of GSK1120212 (Trametinib) and MEK162; and/or the p90RSK-inhibitor is BI-D1870.

In a last aspect, there is provided for a method for the treatment of a cancer selected from the group consisting of NRAS-, KRAS- and BRAF-mutated cancer, preferably NRAS-mutated cancer, preferably melanoma, preferably NRAS-mutated melanoma, wherein the method comprises the simultaneous, separate or sequential administering to a patient of a ROCK-inhibitor and a an inhibitor of a protein of the MAPK/ERK pathway.

Preferably, said inhibitor of a protein of the MAPK/ERK pathway is selected from the group consisting of a RAF-inhibitor, an ERK-inhibitor, a MEK-inhibitor and a p90RSK inhibitor. Preferably, the cancer is melanoma, preferably NRAS-mutated melanoma. Preferably, the ROCK-inhibitor is selected from the group consisting of GSK269962A, Fasudil, RKI-1447, and Y27632; the RAF-inhibitor is selected from the group consisting of PLX4720 (Vemurafenib), and GSK2118436 (Dabrafenib); the ERK-inhibitor is selected from the group consisting of SCH772984 and VTX-11e; the MEK-inhibitor is selected from the group consisting of GSK1120212 (Trametinib) and MEK162; and/or the p90RSK-inhibitor is BI-D1870.

The treatment of the patient includes treatment in the first line or second line, or third line. In particular the disclosure herein can advantageously be used in patients that, e.g. in monotherapy, show reduced response to the use of an MEK-inhibitor, a ERK-inhibitor, a RAF-inhibitor or a p90RSK-inhibitor either from the start, or after a certain period of treatment with the MEK-inhibitor, ERK-inhibitor, RAF-inhibitor or p90RSK-inhibitor, for example patients that are resistant to such inhibitor.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

A list of preferred inhibitors,
BRaf inhibitor: PLX4720 (Vemurafenib), GSK2118436 (Dabrafenib)
MEK inhibitor: GSK1120212 (Trametinib), MEK162
ERK inhibitor: SCH772984, VTX-11e
p90RSK inhibitor: BI-D1870
ROCK inhibitors: GSK269962A, Fasudil, RKI-1447, Y27632

EXAMPLES

Example 1

Summary

Malignant melanoma is a highly aggressive cancer with rising incidence worldwide and, once metastasized, is notoriously difficult to treat. The most commonly mutated genes in cutaneous melanoma are BRAF and NRAS, whereas oncogenic KRAS is also observed in a minority of the cases. Targeted therapies are now used for BRAF, but are lacking for NRAS. MEK inhibitors show promise as drugs for the treatment of NRAS mutant melanoma, but will probably be insufficient as single agents due to a limited response rate, limited durability of response and toxicity issues. In fact, NRAS and BRAF mutant melanoma patients develop resistance to MEK inhibitor MEK162 already after a median of 3.7 and 3.3 months, respectively (Ascierto et al., Lancet Oncol. (2013) 14, 249-256). It is known that intrinsic and acquired resistance to targeted agents limit their therapeutic effects. We identified ROCK inhibitors (e.g. GSK269962A, Fasudil) as sensitizers to inhibitors of the MAPK/ERK pathway, for example a MEK inhibitor (GSK1120212), in a panel of treatment-naïve NRAS mutant melanoma cell lines and show efficacy of the combinations in 2 xenografted lines of this panel.

To model acquired resistance, we created resistant sublines of NRAS mutant melanoma by long-term culture in the presence inhibitors of the MAPK/ERK pathway, for example, 1 µM ERK inhibitor. ERK phosphorylation is required for survival and growth. In sensitive lines MEK or ERK inhibitors inhibit ERK phosphorylation. Therefore, sensitive lines cannot survive or grow in presence of ERK or MEK inhibitors. The resistant sublines we created have reactivated MAPK/ERK pathway signaling, i.e. the levels of phosphorylated p90RSK, directly downstream of ERK in the MAPK/ERK pathway, in the presence of the inhibitors in these resistant sublines are as high as in untreated parental cell lines. Therefore, these resistant sublines are able to survive and grow in the presence of MEK or ERK inhibitors. Interestingly, these sublines are at least as sensitive to ROCK inhibitors as the parental cell lines. The findings support a combination therapy of inhibitors of the MAPK/ERK pathway and ROCK inhibitors for NRAS, KRAS and/or BRAF mutated cancers, in particular NRAS mutant melanoma, both treatment-naïve and with acquired resistance to MAPK/ERK pathway, e.g. ERK, targeting therapies.

We tested various agents alone and in combination with MAPK pathway inhibitors in a panel of treatment-naïve NRAS mutant melanoma lines. The best performing combination enhanced apoptosis (increased caspase 3 and PARP cleavage and BimEL levels), induced cytostasis (abolished expression of cell cycle progression protein Cyclin D1) and reduced phospho-S6RP levels. It also suppressed outgrowth of two xenografted NRAS mutant melanoma cell lines.

Materials and Methods

Inhibitors

We used the MEK inhibitors GSK1120212 (Selleck) and, ERK inhibitor SCH772984 (Merck), pan-p90RSK inhibitor BI-D1870 (Enzo Life Sciences), BRaf inhibitor PLX4720 (Selleck), and ROCK inhibitors Fasudil (Selleck), and GSK269962A (Axon MedChem). Also various other drugs targeting several other pathways and proteins were tested.

Cell Culture and Drug Treatments

Cell line sources: Leiden University Medical Center: Mel 95.03. Other sources: BLM, SK-MEL-147, mel888.

NRAS Mutation: Q61R BLM, SK-MEL-147. BRAF mutation: Mel 95.03, mel 888. All cell lines were cultured in Dulbecco's modified Eagle's Medium (DMEM, Gibco) supplemented with 9% fetal calf serum (Sigma) and 1% glutamine. To generate MEK and ERK inhibitor resistant sublines, cells were plated on 10 cm dishes. Medium containing 1 µM SCH772984 was added the next day and changed twice a week. After 2 weeks colonies were picked and expanded in the presence of the inhibitor. In addition, multiple colonies per 10 cm dish were trypsinized and expanded to obtain resistant pools.

For short-term viability assays of inhibitors, cells were plated in 96-well format and treated on the next day with a dilution range of one inhibitor with or without a second inhibitor with a concentration as mentioned in the figure. After 3 days, cells were incubated with CellTiter-Blue (Promega) and fluorescence was measured with a TECAN Infinite M200 microplate reader. For proliferation assays, equal cell numbers were plated on 6 well dishes. The next day, cells were treated with one or more inhibitors and refreshed with medium with inhibitors every 3-4 days. Cells were stained with crystal violet after 7-11 days of treatment.

For Western blot analysis, cells were plated on 10 cm dishes. Cells were treated on the next day with single inhibitors or combinations thereof and harvested 24 hours later.

Immunoblotting and Antibodies

Cells pellets were lysed in RIPA buffer (50 mM TRIS pH8.0, 150 mM NaCl, 1% Nonidet P40, 0.5% sodium deoxycholate, 0.1% SDS) and the protein concentration was determined using BioRad Protein Assay. Immunoblot analysis was performed using standard techniques on 4-12% Bis-Tris polyacrylamide-SDS gels (NuPAGE). Antibodies used were: phospho-AKT (Ser473, #9271), cleaved caspase 3 (Asp175, #9661), p42/p44 (#9102), phospho-p42/p44 (Thr202/Tyr204, #9106), HSP90 (#4874), MEK (#4694), phospho-MEK (Ser217/221, 41G9, #9154), PARP (#9542), RSK1/2/3 (p90) (#9355), Bax (D2E11, #5023), Bim (C34C5, #2933), Puma (#4976), phospho-Cofilin (Ser3, #3313), Cofilin (#5176), phospho-S6RP (Ser235/236, #4856), phospho-S6RP (Ser240/244, #2215), and S6RP (#2217) (all from Cell Signaling), phospho-RSK1 (p90) (Thr359/Ser363, #04-419, Millipore), alpha-tubulin (DM 1A, Sigma), AKT1/2 (sc-8312), ROCK1 (#611137, Becton Dickinson), Bcl-2 (N19, sc-492) and Cyclin D1 (H295, sc-753) (all from Santa Cruz), p27 (610241, BD Transduction Laboratories), ROCK2 (A300-047A, Bethyl Laboratories). Protein detection for Western blotting was performed by fluorescence detection with the Odyssey reader (LI-COR Biosciences).

ROCK2 Kinase Activity Assay

Treated cells were lysed in NP40 buffer (20 mM HEPES pH 7.4, 175 mM NaCl, 0.7% Nonidet NP-40, 10 mM EDTA. Added before use: 1:25 diluted Roche complete protease inhibitor cocktail, phosphatase inhibitors: 10 mM NaF, 1 mM Na3VO4, 1 mM sodium pyrophosphate, 10 mM beta-glycerophosphate). The lysate was cleared by centrifugation. Sepharose G beads were equilibrated with PBS and 12.5 µl original slurry was used as 50:50 slurry. 500 µg protein at 1-2 µg/µl were precleared with sepharose G beads for 30 min, incubated with 1 µl ROCK2 antibody (A300-047A, Bethyl Laboratories) for 1 h and immunoprecipitated with sepharose G beads over night. The beads are washed 3 times with 0.5 ml kinase buffer (20 mM Tris-HCl pH 7.5, 100 mM KCl2, 5 mM MgCl2, 5 mM MnCl2, added before use: 0.1 mM DTT, 2 mM EDTA). 40 µl kinase buffer with 0.1% beta-mercaptoethanol, 100 µM ATP and 1 µg recombinant human MYPT1 were added to the beads and incubated at 30° C. under agitation. 20 µl SDS sample buffer with beta-mercaptoethanol were added, the samples boiled. Precast SDS-PAGE gels were loaded with 25 µg lysate as input controls and 20 µl of the reaction volume to detect ROCK2 kinase activity, respectively, and blotted onto a nitrocellulose membrane. ROCK1 (611137, Becton Dickinson), ROCK2 (A300-047A, Bethyl Laboratories), alpha tubulin (DM 1A, Sigma Aldrich), and MYPT1 phosphorylation at Thr696 (ABS45, Millipore) were detected and quantified on the same membrane with the Odyssey reader (LI-COR Biosciences).

REFERENCES

NP-40 IP-buffer: Vogel 2008 The role of the mitotic spindle checkpoint in chemotherapy-induced apoptosis (archiv.ub.uni-marburg.de/diss/z2009/0103/pdf/dcv.pdf).

ROCK kinase assay buffer modified from Chun et al. 2011 Am J Physiol Endocrinol Metab In vivo activation of ROCK1 by insulin is impaired in skeletal muscle of humans with type 2 diabetes In Vivo Assays Six to ten week old male NOD/SCID mice were subcutaneously injected with $5*10^5$ cells into both flanks. After the tumors reached a size of 50-150 mm$^3$ mice were treated with 0.05 or 0.1 mg/kg MEK inhibitor (GSK1120212) and/or ROCK inhibitor (GSK266962A, 10 mg/kg). Both GSK1120212 and GSK269962A were applied by oral gavage (in 5% Tween80, 3.25% ethanol, DMSO for GSK1120212 and in 10% Tween80, 6.5% ethanol, 10% DMSO for GSK266962A). Tumors were measured twice a week with a caliper. Tumor volume was calculated by the formula (a*b2)/2, with 'a' being the longest diameter and b' the respective perpendicular diameter of the tumor. Mice were euthanized by $CO_2$ when tumors reached a volume of 1 cm3, according to a protocol approved by the Institutional Animal Experiment Ethics Committee.

Results

Treatment-Naïve NRAS Mutant Melanoma is Sensitive to a Combination of MEK and ROCK Inhibitors To model inhibitor sensitivity of treatment-naïve NRAS mutant melanoma we made use of a panel of human metastatic melanoma cell lines carrying activating mutations in NRAS codon 61 (R, K, N), including cell lines available in the prior art. Some cell lines were part of a large collection of low passage lines generated by the Leiden University Medical Center in The Netherlands. None of the lines have been exposed to targeted agents before explantation. Presence of the NRAS mutation and absence of exon 15 BRAF mutations has been determined by conventional sequencing.

To assess the sensitivity of NRAS mutant melanoma lines to a wide range of targeted therapies, we treated appropriate cell numbers in 96 well format with inhibitors targeting the MAPK pathway (MEK inhibitors GSK1120212, ERK inhibitor SCH772984, pan-p90RSK inhibitor BI-D1870) and various other targets and with ROCK inhibitors Fasudil and GSK269962A for three days and measured viability with the CellTiter-Blue reagent.

The data suggests that in general single inhibitors would likely be insufficient to treat NRAS mutant melanoma. This was confirmed for a subset of cell lines in long-term proliferation assays of 7-11 days in 6-well format (data not shown).

Figure 1B:
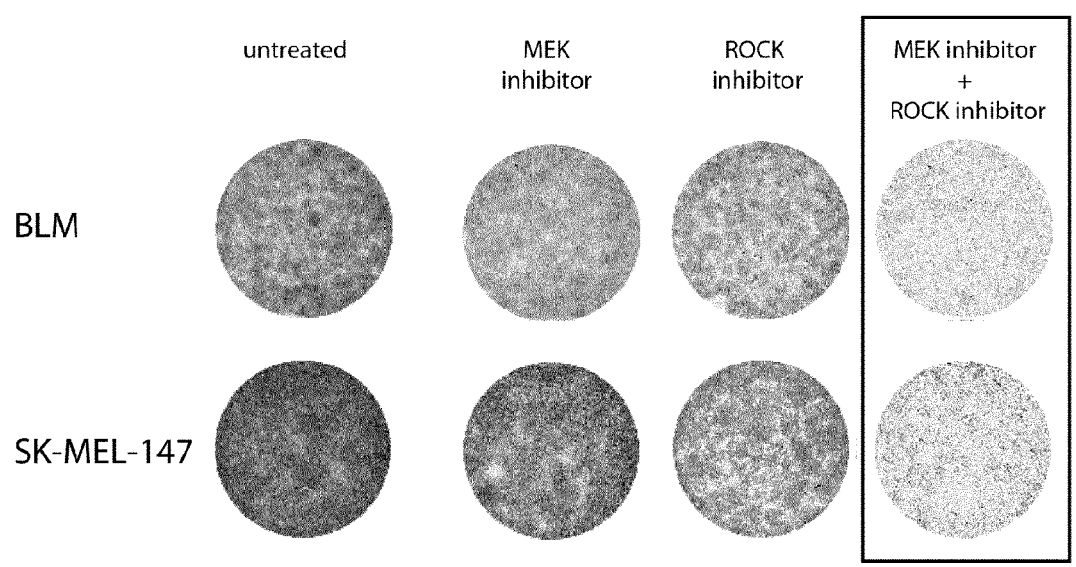
FIG. 1B: Combination of ROCK inhibitor GSK269962A with a MEK inhibitor kills or inhibits NRAS mutant melanoma cell proliferation; Cells were seeded equal densities and treated with GSK1120212 (MEKi) and GSK269962A (ROCKi) as indicated and stained with crystal violet.
Figure 1C:
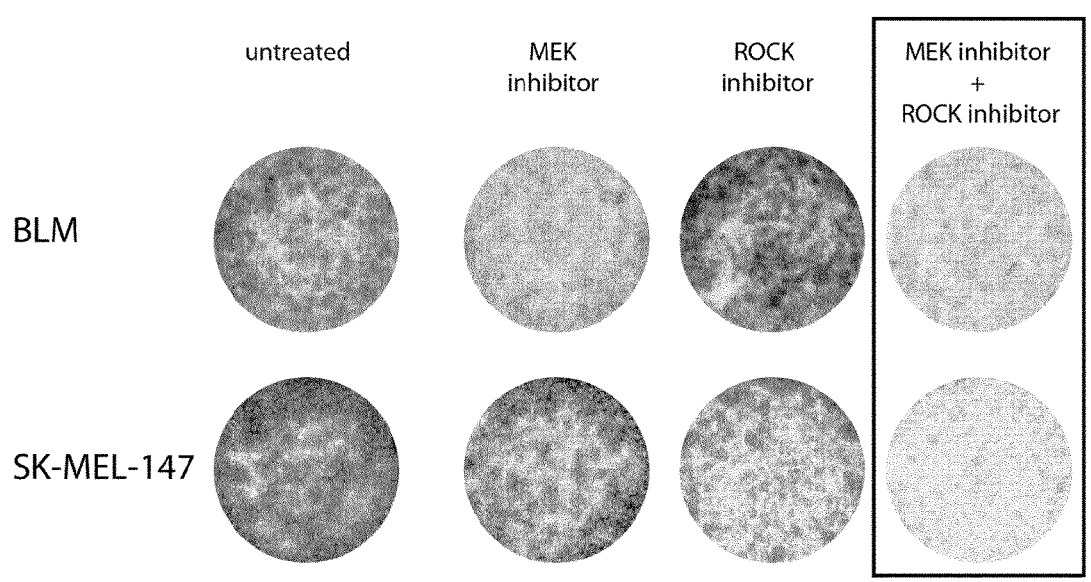
FIG. 1C: Combination of ROCK inhibitor Fasudil with a MEK inhibitor kills or inhibits NRAS mutant melanoma cell proliferation; Cells were seeded equal densities and treated with GSK1120212 (MEKi) and Fasudil (ROCKi) as indicated and stained with crystal violet.

Interestingly, while both ROCK inhibitors showed only modest activity as single agent, used at an $IC_{20}$ concentration they sensitized all tested lines to a broad range of MEK or ERK inhibitor dilutions (1 nM to 10 µM) producing an effect greater than the effect of the individual drugs, in an additive (co-operative) to synergistic fashion in short-term viability assays (FIG. 1A; right two panels) and in long-term proliferation assays (FIG. 1B and FIG. 1C).

The same was true for an $IC_{20}$ concentration of the MEK or ERK inhibitor added to a broad range of ROCK inhibitor dilutions (1 nM to 10 µM, FIG. 1A, left panel and FIG. 1B and FIG. 1C). Note that the individual inhibitor concentrations were titrated to have little effect on their own (in the low nanomolar range for MEK inhibitor GSK1120212), but produce an effect greater than the effect of the individual drugs, in an additive (co-operative) to synergistic fashion upon combination (FIG. 1B and FIG. 1C). We also observed an effect of the combination of MEK inhibitor and ROCK inhibitor greater than that of the individual drugs on the proliferation of BRAF mutant cell lines (FIG. 1D).

Figure 2A:
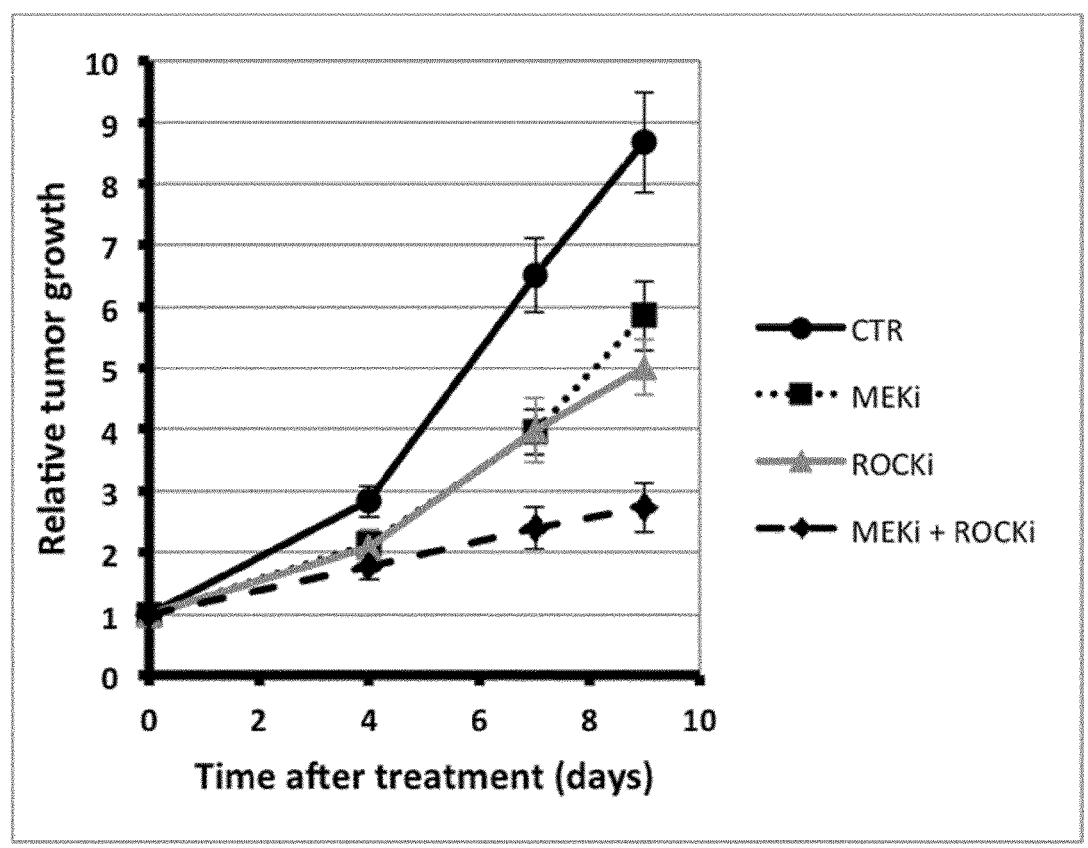
FIG. 2A: Treatment-naïve NRAS mutant melanoma is sensitive to the combination of MEK and ROCK inhibitors in vivo; ROCK inhibitor increases MEK-inhibitor induced effects on tumor growth in vivo at low doses of MEK inhibitor. Melanoma cells ($5*10^5$ SK-MEL-147) were subcutaneously injected into both flanks of NOD/SCID mice. Tumor sizes were measured with a caliper and tumor volume was calculated by the formula $(a*b^2)/2$ with 'a' being the longest diameter and 'b' the respective perpendicular diameter of the tumor. After the tumors reached a size of 20-100 mm3, mice received by oral gavage either vehicle, GSK1120212 (MEKi), (0.05 mg/kg), 10 mg/kg GSK269962A (ROCKi) or both drugs. N=10 for each group, except for ROCKi n=8. Error bars represent standard error of the mean (SEM).
Figure 2B:
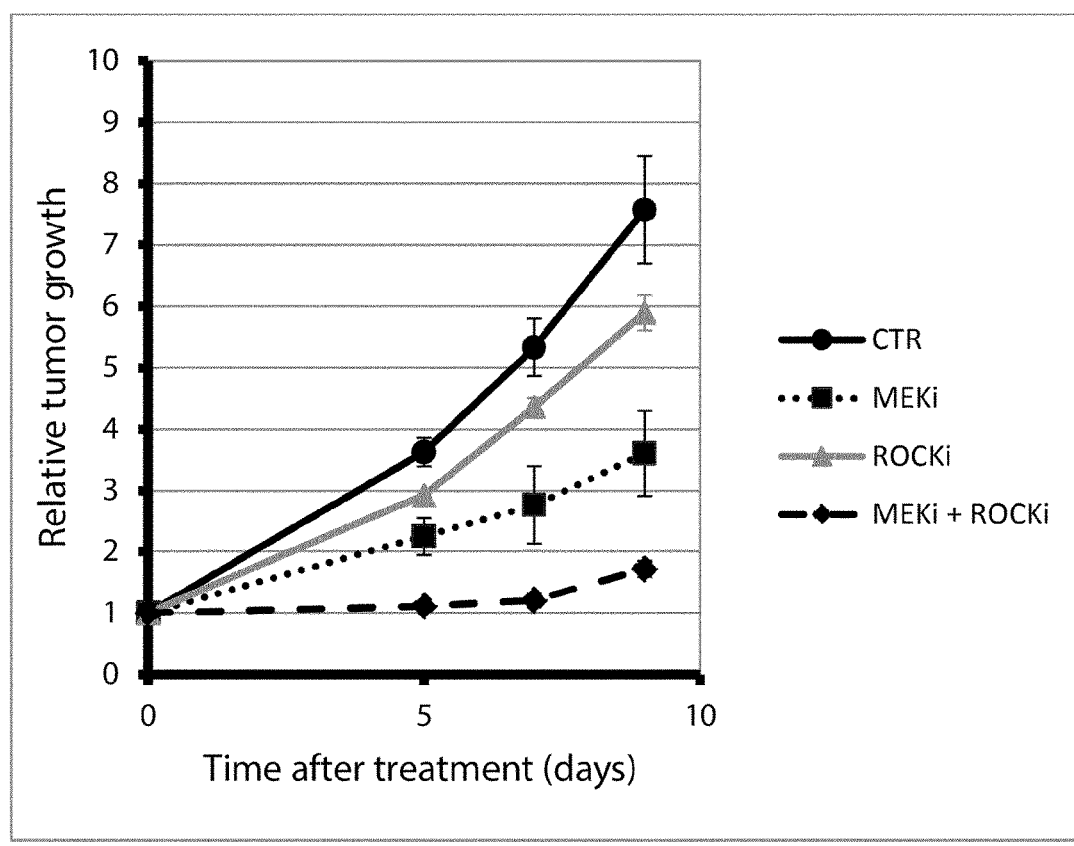
FIG. 2B: Treatment-naïve NRAS mutant melanoma is sensitive to the combination of MEK and ROCK inhibitors in vivo; ROCK inhibitor increases MEK-inhibitor induced effects on tumor growth in vivo at low doses of MEK inhibitor. Melanoma cells ($5*10^5$ BLM) were subcutaneously injected into both flanks of NOD/SCID mice. Tumor sizes were measured with a caliper and tumor volume was calculated by the formula $(a*b^2)/2$ with a being the longest diameter and b the respective perpendicular diameter of the tumor. After the tumors reached a size of 20-100 mm3, mice received by oral gavage either vehicle, GSK1120212 (MEKi), (0.1 mg/kg), 10 mg/kg GSK269962A (ROCKi) or both drugs. N=8 for each group, except for ROCKi n=6. Error bars represent standard error of the mean (SEM).

Treatment-Naïve NRAS Mutant Melanoma is Sensitive to the Combination of MEK and ROCK Inhibitors In Vivo The in vitro results suggested that a combination therapy of MAPK/ERK-pathway inhibitors, like MEK inhibitors, and ROCK inhibitors can be more effective in the treatment of, for example, NRAS mutant cancers including melanoma, as well as KRAS and BRAF mutant cancers, including melanoma, than the administration of single agents. To test this hypothesis in vivo, we injected $5 \times 10^5$ NRAS mutant melanoma cells SK-MEL-147 into both flanks of immunocompromised mice. We waited until the tumors reached a size of 50-150 $mm^3$ before starting treatment. MEK inhibitor GSK1120212 was administered once daily at a dose of 0.05 mg/kg by oral gavage. ROCK inhibitor GSK269962A was administered once daily at a dose of 10 mg/kg by oral gavage. Unless otherwise stated, all groups consisted of 5 animals, i.e. 10 tumors per group. Mice were sacrificed when the tumour reached a size of 1 $cm^3$. We have dosed the MEK and ROCK inhibitors so lowly that they have only a weak effect as single agents, but the benefit of the combination becomes apparent (FIG. 2A). The groups of single agent treated mice had to be sacrificed at the same time as the control group, but the combination treatment prolonged survival of the mice by 8 days, almost doubling their survival time. We also observed the same effect in a xenograft from a different NRAS mutant melanoma cell line, BLM, which was treated with a slightly higher dose of MEK inhibitor (FIG. 2B).

MEK or ERK Inhibitor Resistant Sublines of NRAS Mutant Melanoma are Sensitive to a Combination of MEK or ERK and ROCK Inhibitors.

To model resistance of e.g. NRAS mutant melanoma to agents targeting the MAPK pathway, we generated sublines resistant to ERK inhibitor SCH772984. We seeded multiple cell lines on 10 cm dishes and changed the culture medium containing 1 µM of the ERK inhibitor twice a week. After 2 weeks small colonies of a few cells with different morphology from the surrounding cells with senescence-like flat and broad morphology were picked and propagated. In addition, pools of resistant cells were generated by collecting the cells from colonies by short trypsinization, which left the senescent-like cells on the plate.

Initial characterization of ERK inhibitor resistant sublines of BLM indicated a much reduced sensitivity to the MEK or ERK inhibitor across all doses, with a significantly increased residual population. Interestingly, the ERK inhibitor resistant sublines were as sensitive to the dual $PI_3K$/mTOR inhibitor PI-103 as the parental line, suggesting no increased dependence on the $PI_3K$ pathway. We assessed sensitivity to a panel of other inhibitors including ROCK inhibitors but observed mainly slight differences.

Figure 3:
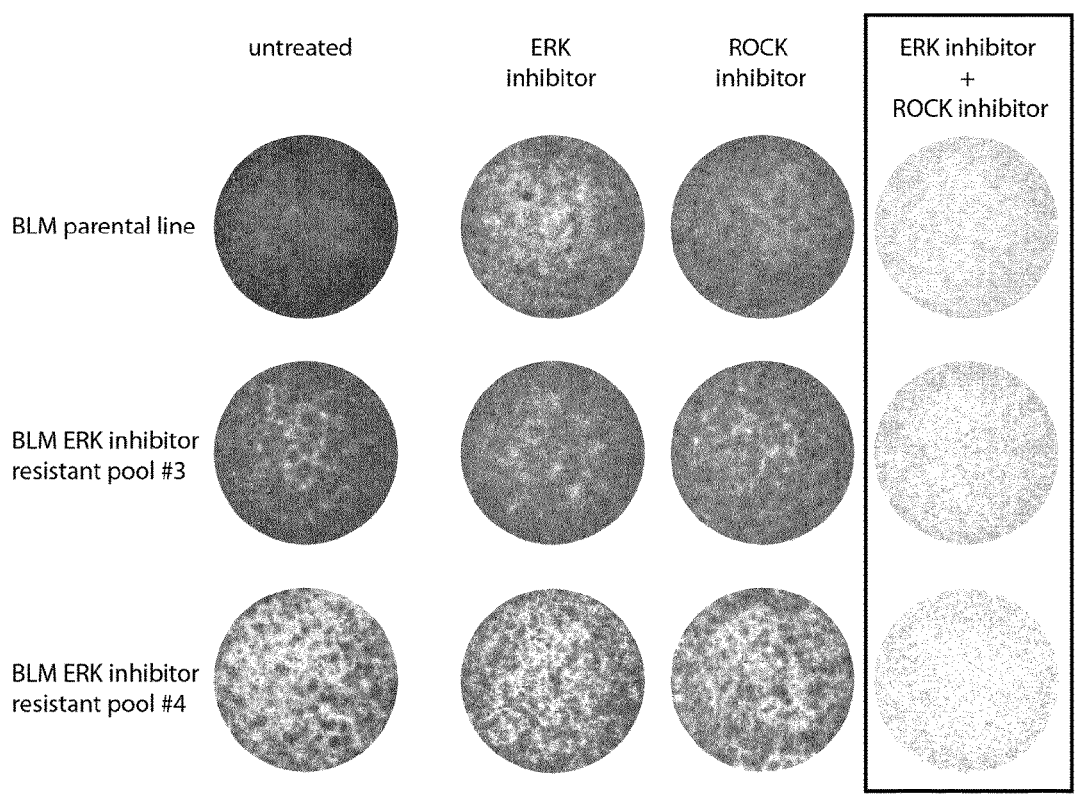
FIG. 3: An ERK inhibitor resistant derivative of a NRAS mutant melanoma line is sensitive to combinations of ERK inhibitor with ROCK inhibitor; Cells were seeded equal densities and treated with SCH772984 (ERKi) and GSK269962A ROCKi) as indicated and stained with crystal violet. Inhibitor concentrations (cell line, ERK inhibitor SCH772984, ROCK inhibitor GSK269962A): BLM parental, 0.25 µM, 2 µM; BLM ERK inhibitor resistant pool #3 2.5 µM (10× of parental), 2 µM; BLM ERK inhibitor resistant pool #4, 2.5 µM (10× of parental), 2 µM.

These findings suggested that not only treatment-naïve NRAS mutant melanoma, but also NRAS mutant melanoma with an acquired resistance to MAPK pathway inhibitors could be amenable to combination treatment with MEK and ROCK inhibitors. Indeed, similarly to the parental line BLM, which shows a beneficial effect of the combination of MEK or ERK and ROCK inhibitors on cell viability in short- and long-term assays, also the ERK inhibitor resistant pools respond to the combination of ERK and a ROCK inhibitor (FIG. 3).

The invention claimed is:

1. A method for the treatment of a cancer selected from the group consisting of NRAS-, KRAS- and BRAF-mutated cancer, wherein the method comprises administering to a patient in need thereof a ROCK-inhibitor and an inhibitor of a protein of the MAPK/ERK pathway.

2. The method of claim 1, wherein said inhibitor of a protein of the MAPK/ERK pathway is selected from the group consisting of a RAF-inhibitor, an ERK-inhibitor, a MEK-inhibitor, and a p90RSK-inhibitor.

3. The method of claim 1, wherein the cancer is melanoma.

4. The method of claim 2, wherein
   a. the ROCK-inhibitor is selected from the group consisting of GSK269962A, Fasudil, RKI-1447, and Y27632;
   b. the RAF-inhibitor is selected from the group consisting of PLX4720 (Vemurafenib), and GSK2118436 (Dabrafenib);
   c. the ERK-inhibitor is selected from the group consisting of SCH772984 and VTX-11e;
   d. the MEK-inhibitor is selected from the group consisting of GSK1120212 (Trametinib) and MEK162; and/or
   e. the p90RSK-inhibitor is BI-D1870.

5. The method of claim 1, wherein the ROCK-inhibitor is administered simultaneously, separately or sequentially with said inhibitor of a protein of the MAPK/ERK pathway.

6. The method of claim 2, wherein the RAF-inhibitor is administered simultaneously, separately or sequentially with said ROCK-inhibitor.

7. The method of claim 2, wherein the ERK-inhibitor is administered simultaneously, separately or sequentially with a ROCK-inhibitor.

8. The method of claim 2, wherein the MEK-inhibitor is administered simultaneously, separately or sequentially with said ROCK-inhibitor.

9. The method of claim 2, wherein the p90RSK-inhibitor is administered simultaneously, separately or sequentially with a ROCK-inhibitor.

10. The method of claim 1, wherein the cancer is a NRAS-mutated melanoma resistant to a RAF-inhibitor, an ERK-inhibitor, a MEK-inhibitor and/or a p90RSK-inhibitor.

11. A method for the treatment of a cancer selected from the group consisting of NRAS-, KRAS- and BRAF-mutated cancer, wherein the method comprises the simultaneous, separate or sequential administering to a patient in need thereof a product comprising a ROCK-inhibitor and an inhibitor of a protein of the MAPK/ERK pathway, as a combined preparation.

12. The method of claim 11, wherein said inhibitor of a protein of the MAPK/ERK pathway is selected from the group consisting of a RAF-inhibitor, an ERK-inhibitor, a MEK-inhibitor and a p90RSK-inhibitor.

13. The method of claim 11, wherein the cancer is melanoma.

14. The method of claim 11, wherein the cancer is a NRAS-mutated melanoma resistant to a RAF-inhibitor, an ERK-inhibitor, a MEK-inhibitor and/or a p90RSK-inhibitor.

15. The method of claim 12, wherein
  a. the ROCK-inhibitor is selected from the group consisting of GSK269962A, Fasudil, RKI-1447, and Y27632;
  b. the RAF-inhibitor is selected from the group consisting of PLX4720 (Vemurafenib), and GSK2118436 (Dabrafenib);
  c. the ERK-inhibitor is selected from the group consisting of SCH772984 and VTX-11e;
  d. the MEK-inhibitor is selected from the group consisting of GSK1120212 (Trametinib) and MEK162; and/or
  e. the p90RSK-inhibitor is BI-D1870.

* * * * *